(12) United States Patent
DiMagno et al.

(10) Patent No.: US 10,053,423 B2
(45) Date of Patent: Aug. 21, 2018

(54) RADIOIODINATED COMPOUNDS

(71) Applicant: NUtech Ventures, Lincoln, NE (US)

(72) Inventors: Stephen DiMagno, Chicago, IL (US); Bao Hu, Lincoln, NE (US)

(73) Assignee: NUtech Ventures, Lincoln, NE (US)

( * ) Notice: Subject to any disclaimer, the term of this patent is extended or adjusted under 35 U.S.C. 154(b) by 0 days.

(21) Appl. No.: 15/109,608

(22) PCT Filed: Jan. 2, 2015

(86) PCT No.: PCT/US2015/010048
§ 371 (c)(1),
(2) Date: Jul. 1, 2016

(87) PCT Pub. No.: WO2015/147950
PCT Pub. Date: Oct. 1, 2015

(65) Prior Publication Data
US 2016/0326109 A1    Nov. 10, 2016

Related U.S. Application Data

(60) Provisional application No. 61/923,541, filed on Jan. 3, 2014.

(51) Int. Cl.
| | | |
|---|---|---|
| *C07D 251/08* | (2006.01) | |
| *C07D 207/404* | (2006.01) | |
| *C07D 207/46* | (2006.01) | |
| *C07C 227/16* | (2006.01) | |
| *C07D 207/40* | (2006.01) | |
| *A61K 51/04* | (2006.01) | |
| *C07D 231/12* | (2006.01) | |

(52) U.S. Cl.
CPC ............ *C07D 207/40* (2013.01); *A61K 51/04* (2013.01); *C07C 227/16* (2013.01); *C07D 207/404* (2013.01); *C07D 207/46* (2013.01); *C07D 231/12* (2013.01); *C07D 251/08* (2013.01)

(58) Field of Classification Search
CPC .. C07D 251/08; C07D 207/404; C07C 227/16
USPC ............................ 544/216; 548/545; 570/261
See application file for complete search history.

(56) References Cited

U.S. PATENT DOCUMENTS

| | | | |
|---|---|---|---|
| 8,377,704 B2 * | 2/2013 | DiMagno | G01N 33/84 |
| | | | 436/100 |
| 8,604,213 B2 * | 12/2013 | Dimagno | 546/330 |
| 2007/0092441 A1 | 4/2007 | Wadsworth et al. | |
| 2012/0004417 A1 * | 1/2012 | Dimagno | C07C 41/18 |
| | | | 546/330 |
| 2014/0121371 A1 * | 5/2014 | DiMagno | C07D 207/448 |
| | | | 544/174 |

FOREIGN PATENT DOCUMENTS

| | | |
|---|---|---|
| WO | WO 2010/048170 | 4/2010 |
| WO | WO 2013/003734 | 1/2013 |
| WO | WO 2013/184484 | 12/2013 |

OTHER PUBLICATIONS

Hansch et al., "A survey of Hammett substituent constants and resonance and field parameters," Chem. Rev., 1991, 91 (2): 165-195.
Joong-Hyun and Pike, "Single-step Radiosyntheses of '18F-Labeled Click Synthons' from Azide-functionalized Diaryliodonium Salts," J. Org. Chem., Aug. 2012, 4541-4547.
Seevers and Counsell, "Radioiodination techniques for small organic molecules," Chemical Reviews, 1982, 82(6):.575-590.
Sun and DiMagno, "Room-Temperature Nucleophilic Aromatic Fluorination: Experimental and Theoretical Studies," Angew. Chem., Mar. 2006, 118(17): 2786-2791.
Sun et al., "Ion pairing of "weakly-coordinated" fluoride salts," Chemistry Today, 2008, 26:4-6.
Extended European Search Report in European Application No. 15769853.1, dated May 17, 2017, 7 pages.
Amartey et al., "An efficient batch preparation of high speci TM c activity [123I] and [124I] mIBG," Applied Radiation and Isotopes, Jan. 2001, 54: 711-714.

* cited by examiner

*Primary Examiner* — Venkataraman Balasubramanian
(74) *Attorney, Agent, or Firm* — Fish & Richardson P.C.

(57) ABSTRACT

This disclosure relates to reagents and methods useful in the synthesis of aryl iodines, for example, in the preparation of iodine labeled radiotracers. The reagents and methods provided herein may be used to access a broad range of compounds, including aromatic compounds, heteroaromatic compounds, amino acids, nucleotides, and synthetic compounds.

19 Claims, 1 Drawing Sheet

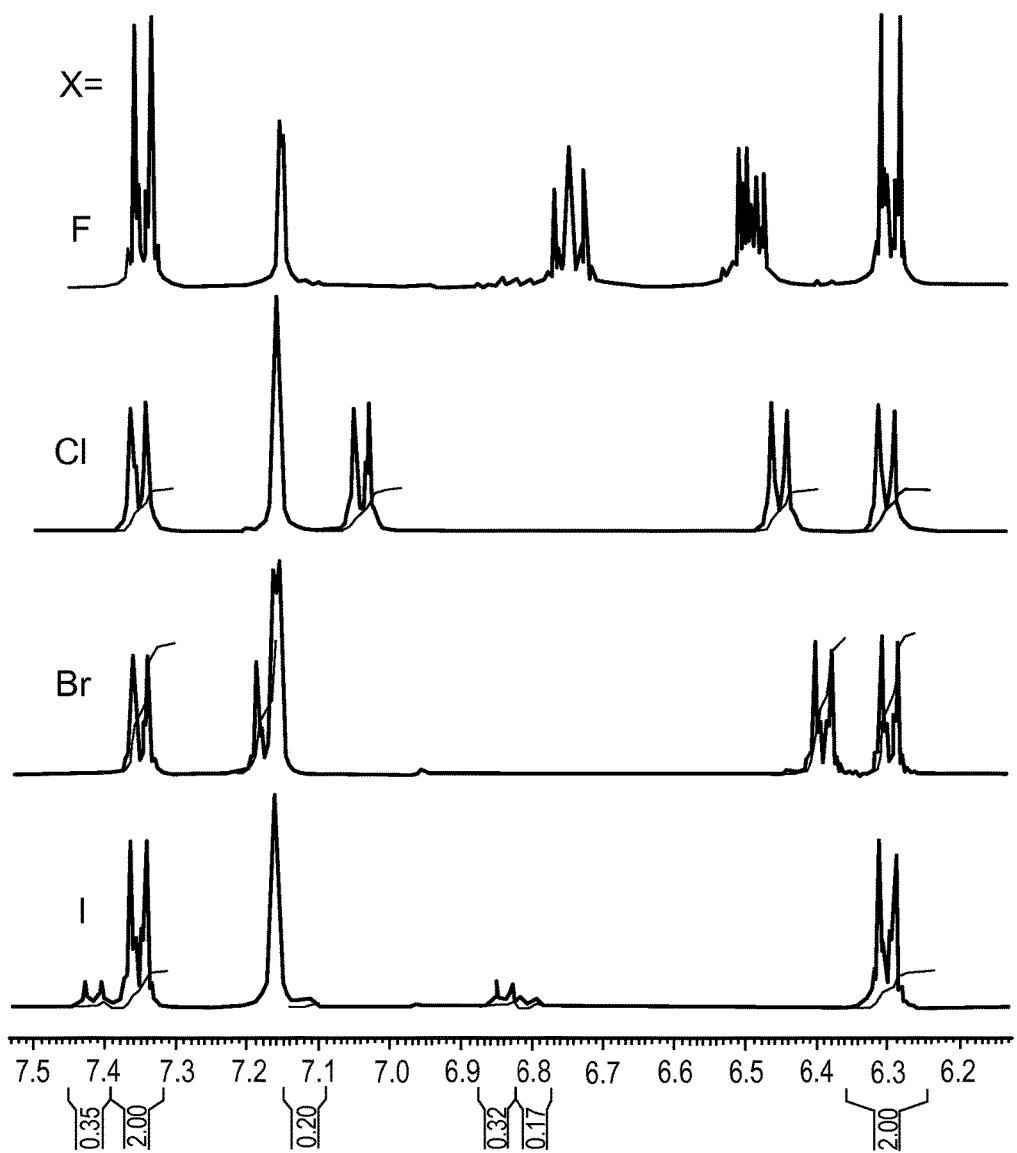

RADIOIODINATED COMPOUNDS

CROSS-REFERENCE TO RELATED APPLICATIONS

This application is a National Stage application under 35 U.S.C. § 371 of International Application No. PCT/US2015/010048, filed Jan. 2, 2015, which claims the benefit of U.S. Provisional Application No. 61/923,541, filed Jan. 3, 2014. The disclosures of the prior applications are incorporated by reference in their entirety.

FEDERALLY SPONSORED RESEARCH OR DEVELOPMENT

This invention was made with Government support under Grant No. R01 EB015536 awarded by the National Institutes of Health. The Government has certain rights in the invention.

TECHNICAL FIELD

This disclosure relates to reagents and methods useful in the synthesis of aryl iodides, for example, in the preparation of iodine-labeled compounds for imaging and therapy. The reagents and methods provided herein may be used to access a broad range of compounds, including aromatic compounds, heteroaromatic compounds, amino acids, nucleotides, polypeptides, and synthetic compounds.

BACKGROUND

Meta-iodobenzylguanidine (MIBG) is a functional analogue of norepinephrine; it is taken up in tissues expressing large amounts of norepinephrine transporter. Such tissues include normal sympathetically innervated organs such as the heart and tumors that are neural crest or neuroendocrine in origin. MIBG was originally developed in the 1970s to image the adrenal medulla. The Food and Drug Administration approved $^{131}$I-MIBG, or iobenguane, as a tumor imaging agent in 1994, and $^{123}$I-MIBG, or AdreView™, was approved for tumor imaging in 2008. Commercial formulations of radioiodinated MIBG contain large amounts of added carrier ($^{131}$I-MIBG specific activity (SA)=1 mCi/μmol, AdreView™ $^{123}$I-MIBG: SA=1 mCi/mmol), because their syntheses rely on isotopic exchange with a relatively large mass of unlabeled "cold" $^{127}$I-MIBG. "Cold" MIBG can compete with radiolabeled MIBG for binding to the norepinephrine transporter (NET), resulting in reduced uptake by sympathetically innervated tissues such as the heart and neuroendocrine tumors. This is particularly a problem for therapeutic doses of $^{131}$I-MIBG; low specific activity MIBG has greater potential to saturate the uptake process in tumor cells, leading to a less potent radiotherapy. In addition, administration of the large mass of the biogenic amine $^{127}$I-MIBG in a therapeutic dose of low specific activity $^{131}$I-MIBG is associated with pharmacological effects, and must be performed by automated slow infusion (~1 hour) to mitigate adverse drug reactions.

SUMMARY

Provided herein are methods of preparing substituted aryl and heteroaryl ring systems using diaryliodonium compounds and intermediates. For example, diaryliodonium salts and diaryliodonium iodides, as provided herein, can undergo decomposition to prepare radiolabeled aryl iodides.

In some embodiments, a method for making a compound of Formula (1):

  (1)

wherein:
Ar$^2$ is an aryl or heteroaryl ring system; and
I* is a radioactive isotope of iodine;
includes (a) reacting a mixture comprising a compound M*I, wherein M is a counter cation, and a compound of Formula (2):

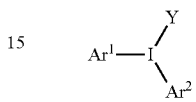  (2)

wherein:
Ar$^1$ is an aryl or heteroaryl ring system that is electron-rich as compared to Ar$^2$;
Y is a leaving group; and
Ar$^2$ is as defined above; and
(b) heating the reaction mixture from step (a).

In some embodiments, the reaction mixture in step (a) further comprises a solvent. For example, the solvent can be an aprotic solvent (e.g., a polar solvent, a nonpolar solvent, or a mixture thereof).

In some embodiments, the specific activity of the radioactive isotope of iodine is at least about 10 mCi/mg.

Also provided herein are compounds of Formula (3):

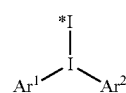  (3)

wherein:
Ar$^1$ is an aryl or heteroaryl ring system that is electron-rich as compared to Ar$^2$;
Ar$^2$ is an aryl or heteroaryl ring system; and
*I is a radioactive isotope of iodine.

Non-limiting examples of such compounds include:

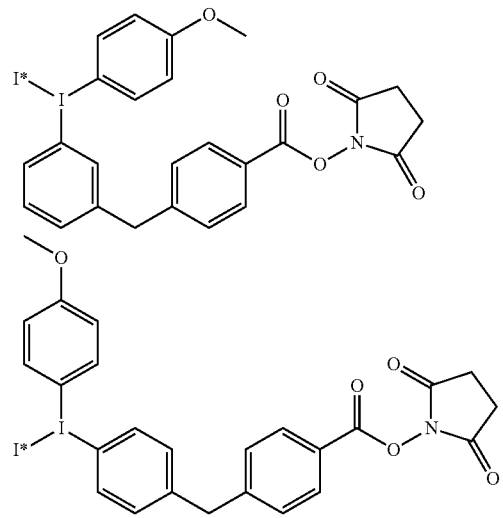

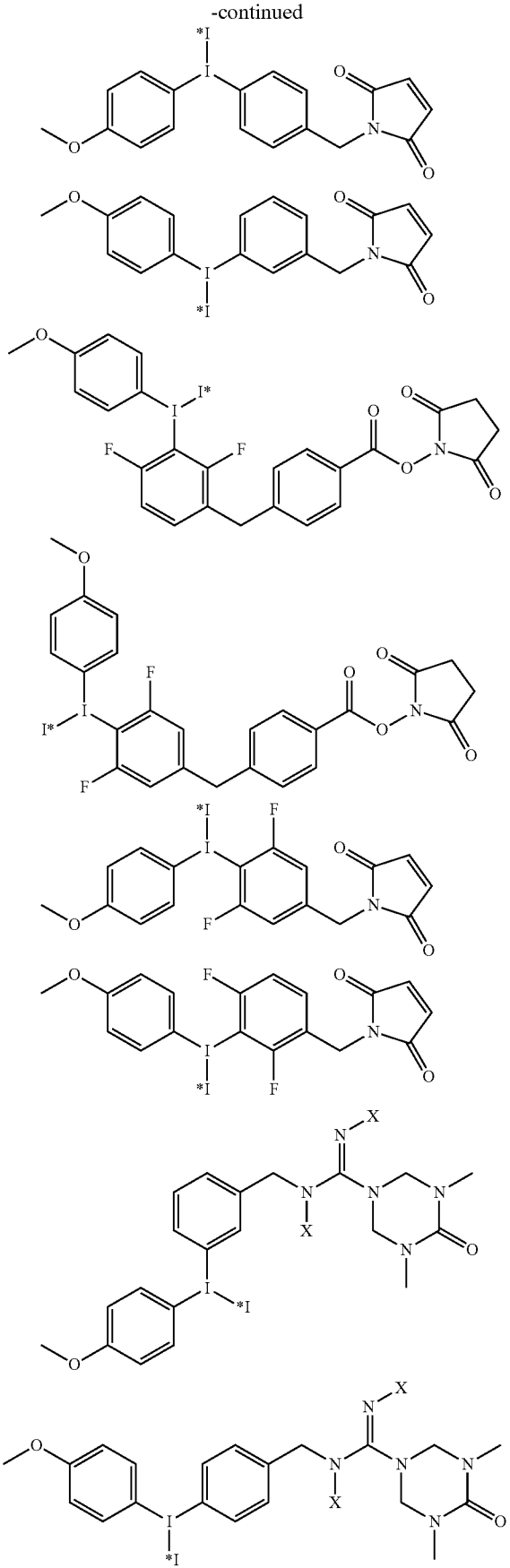
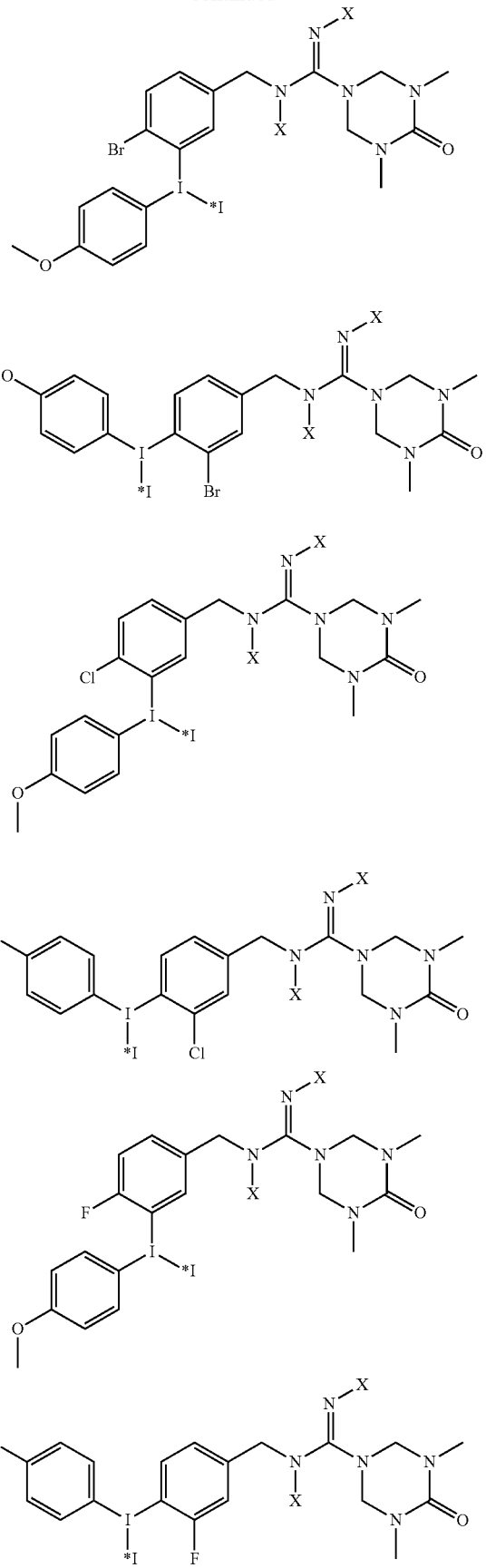

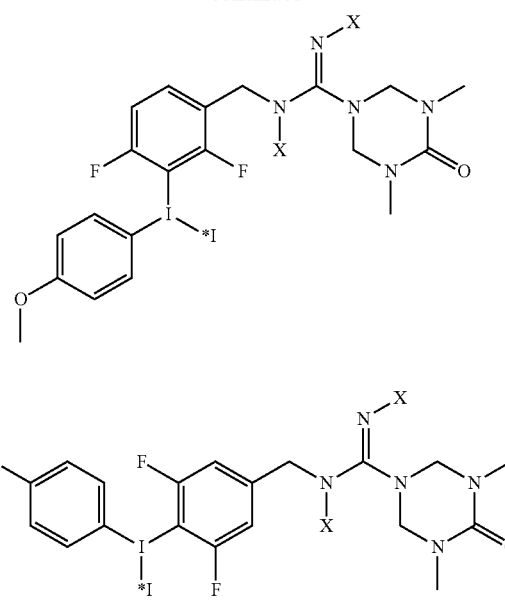
wherein each Y is independently a leaving group as defined above; and
each X is independently a protecting group.
In some embodiments, a compound of Formula (3) can be selected from the group consisting of:
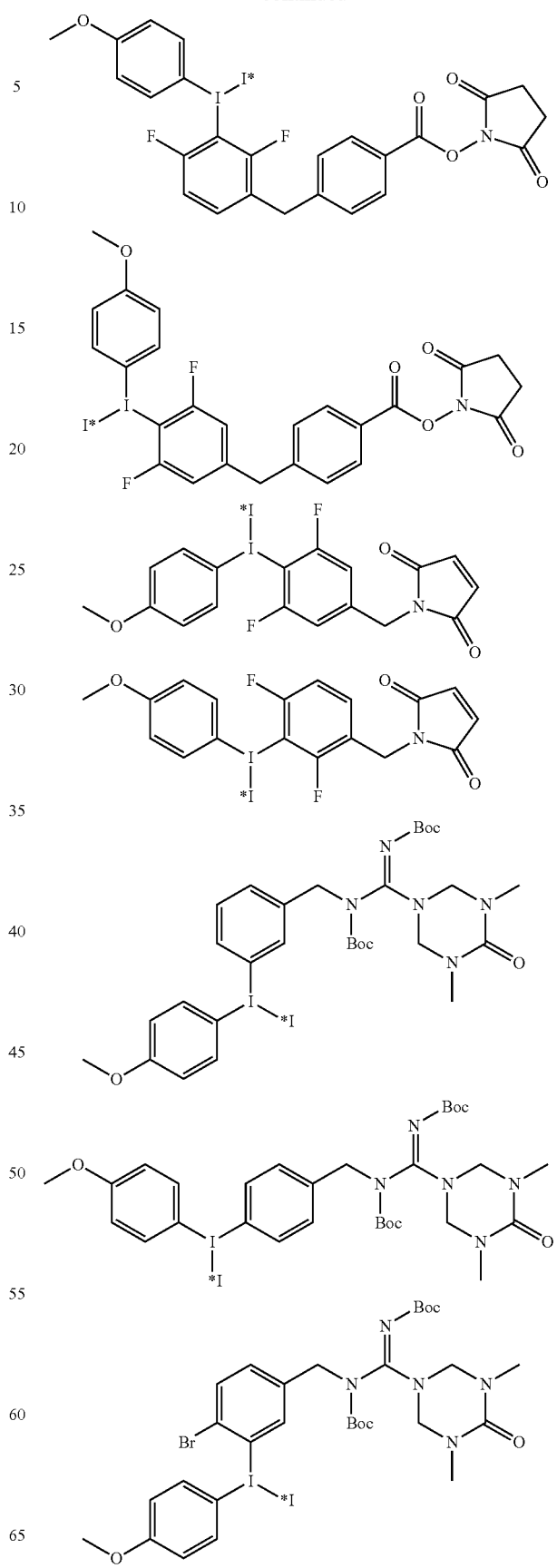

-continued

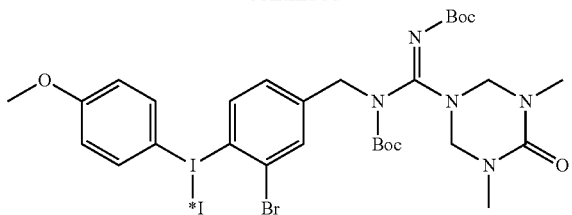

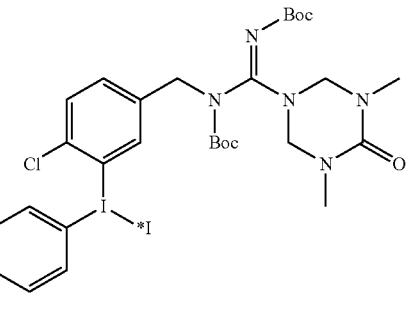

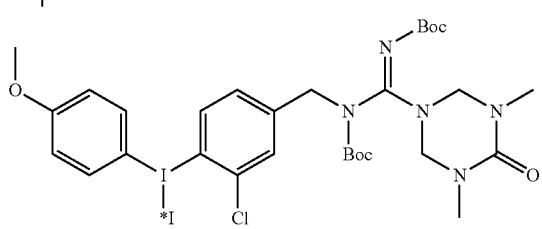

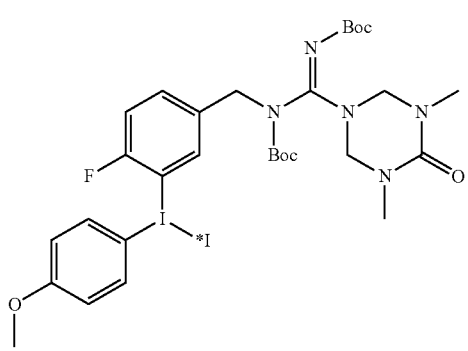

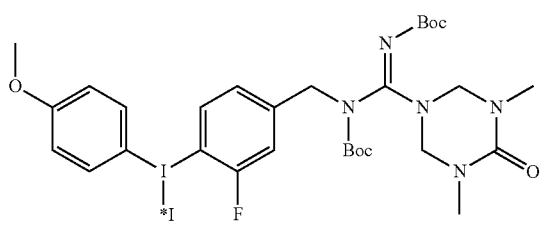

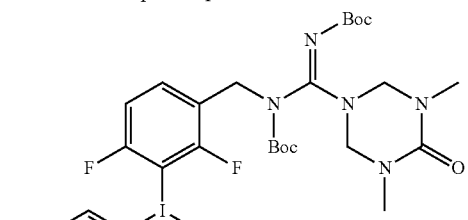

-continued

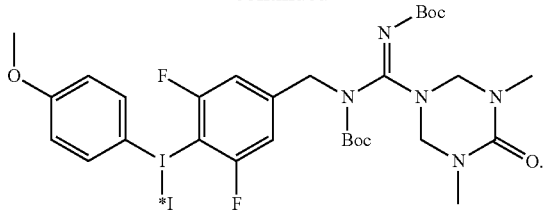 [SMILES: COc1ccc(I(OS(=O)(=O)C(F)(F)F)c2c(F)cc(CN(C(=O)OC(C)(C)C)/C(=N/C(=O)OC(C)(C)C)N3CN(C)C(=O)N(C)C3)cc2F)cc1]

Also provided herein is a method for making a compound of Formula (1)

$$Ar^2—I \qquad (1)$$

wherein:
Ar$^2$ is an aryl or heteroaryl ring system; and
*I is a radioactive isotope of iodine;
the method comprising heating a compound of Formula (3):

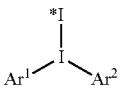

$$(3)$$

wherein:
Ar$^1$ is an aryl or heteroaryl ring system that is electron-rich as compared to Ar$^2$; and
Ar$^2$ is as defined above.

This disclosure further provides a kit comprising a compound of Formula (2). In some embodiments, the kit further comprises a purified solvent. In some embodiments, the kit further comprises one or more chromatography cartridge. In some embodiments, the kit further comprises an acidic reagent.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and FIGURES, and from the claims.

DESCRIPTION OF DRAWINGS

FIG. 1 provides a representative 1H NMR spectra comparing iodination of diaryliodonium salts with fluorination, chlorination, and bromination.

DETAILED DESCRIPTION

Definitions

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

As used herein, the singular forms "a," "an," and "the" include plural referents unless the context clearly dictates otherwise.

The term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond, respectively. In some embodiments, an alkyl, alkenyl, and/or alkynyl group can be substituted with a halogen, such as fluorine, to result in the preparation of a "haloalkyl".

In general, the term "aryl" includes groups comprising a ring structure having aromatic character, including rings with 5 to 14 carbon atoms (e.g., 5- and 6-membered single-ring aromatic groups, such as benzene and phenyl). Furthermore, the term "aryl" includes polycyclic aryl groups, e.g., tricyclic, bicyclic, such as naphthalene and anthracene. The aryl groups can be substituted or unsubstituted.

The term "heteroaryl" includes groups comprising a ring structure having aromatic character, including rings with 5 to 14 atoms (e.g., 5- and 6-membered single-ring aromatic groups) that have from one to four heteroatoms, for example, pyrrole, furan, thiophene, thiazole, isothiaozole, imidazole, triazole, tetrazole, pyrazole, oxazole, isooxazole, pyridine, pyrazine, pyridazine, and pyrimidine, and the like. Furthermore, the term "heteroaryl" includes polycyclic heteroaryl groups, e.g., tricyclic, bicyclic, such as benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, indazole, or indolizine. The heteroaryl groups can be substituted or unsubstituted.

The terms "carbocycle", "carbocyclyl", and "cycloalkyl" as used herein, refer to a 3- to 7-membered non-aromatic substituted or unsubstituted ring in which each atom of the ring is carbon. The terms "carbocycle", "carbocyclyl", and "cycloalkyl" also include polycyclic ring systems having two or more cyclic rings in which two or more carbons are common to two adjoining rings wherein at least one of the rings is carbocyclic, e.g., the other cyclic rings can be cycloalkyls, cycloalkenyls, cycloalkynyls, aryls, heteroaryls, and/or heterocyclyls. Carbocyclyls include cyclopropyl, cyclopentyl, cyclohexyl, cyclohexylmethyl, and 4-methylcyclohexyl. Examples of polycyclic carbocyclyls include bicyclo[2.2.1]heptanyl, norbornyl, and adamantyl.

The term "heterocyclyl" or "heterocyclic group" refers to substituted or unsubstituted non-aromatic 3- to 10-membered ring structures, for example, 3- to 7-membered rings, whose ring structures include one to four heteroatoms. The term "heterocyclyl" or "heterocyclic group" also includes polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "substituted" means that an atom or group of atoms formally replaces hydrogen as a "substituent" attached to another group. For aryl and heteroaryl groups, the term "substituted", unless otherwise indicated, refers to any level of substitution, namely mono, di, tri, tetra, or penta substitution, where such substitution is permitted. The substituents are independently selected, and substitution may be at any chemically accessible position. Substituents can include, for example, an alkyl, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a carbocyclyl, a heterocyclyl, an aralkyl, a heteroaralkyl, or an aromatic or heteroaromatic moiety. It will be understood by those skilled in the art that the moieties substituted on the hydrocarbon chain can themselves be substituted, if appropriate.

The compounds provided herein may encompass various stereochemical forms and tautomers. The compounds also encompasses diastereomers as well as optical isomers, e.g. mixtures of enantiomers including racemic mixtures, as well as individual enantiomers and diastereomers, which arise as a consequence of structural asymmetry in certain compounds. Separation of the individual isomers or selective synthesis of the individual isomers is accomplished by application of various methods which are well known to practitioners in the art.

The term "electron rich", as used herein, refers to an aryl or heteroaryl ring system which is more easily oxidized as compared to a reference ring system. In some embodiments, an electron rich ring system is more easily oxidized as compared to benzene. In some embodiments, aryl or heteroaryl ring system may be substituted with one or more substituents having a Hammett $\sigma_p$ value of less than zero.

Methods of Preparing Substituted Aryl and Heteroaryl Ring Systems Provided herein are methods of preparing substituted aryl and heteroaryl ring systems using diaryliodonium compounds and intermediates. For example, diaryliodonium salts and diaryliodonium iodides, as provided herein, can undergo decomposition to prepare radiolabeled aryl iodides.

Methods for preparing fluorinated compounds using diaryliodonium salts are described in WO 2013/184484; WO 2013/003734; and WO 2010/048170.

Fluoride is the simplest unary fluorine anion and while multiple fluorine isotopes are known, only $^{19}$F is stable. The radioisotope $^{18}$F has a half-life of 109.8 minutes and emits positrons during radioactive decay. Structurally, and to some extent chemically, the fluoride ion resembles the hydroxide ion. Fluoride is the conjugate base of a relatively weak acid and is therefore a hard nucleophile. Because it is the smallest monoanion, fluoride forms salts that feature strong, highly ionic bonds. Moreover, fluoride forms exceptionally strong covalent bonds to other atoms, for example the C—F bond energy in methyl fluoride is approximately 115 kcal/mol, while the C—I bond in methyl iodide is approximately 58 kcal/mol. The high reactivity of fluoride in diaryl iodonium salts results from a combination of strong ion-pairing energy with I(III) cations, and the high strength of aromatic C—F bond in the product. The small size and high electronegativity of the F atom account for many of the differences between fluorine and the other halogens. Ion-pairing energies for fluoride ion are larger than those of the other halogens, and these ion-pairing interactions are the key factors that determine the kinetics and thermodynamics of reactions involving fluoride transfer in solution. (Ion pairing of "weakly-coordinated" fluoride salts H. Sun, B. Wang, and S. G. DiMagno, *Chemistry Today*, 2008, 26, 4-6; Room-Temperature Nucleophilic Aromatic Fluorination: Experimental and Theoretical Studies, H. Sun and S. G. DiMagno, *Angew. Chem. Int. Ed.* 2006, 45, 2720-2725. Also *Angew. Chem.* 2006, 118, 2786-2791). The high electronegativity of fluoride also means that it typically does not act as a reducing agent as the standard reduction potential of fluoride (−2.87 V) is beyond the range of almost all chemical oxidants ($F_2$ is an extraordinarily potent oxidant).

Iodide is one of the largest monatomic anions. It is assigned a radius of around 206 picometers. For comparison, the lighter halides are considerably smaller: bromide (196 pm), chloride (181 pm), and fluoride (133 pm). In part because of its size, iodide forms relatively weak bonds with most elements. It is the conjugate base of a strong acid and is therefore likely to bind much more poorly than other nucleophiles, including the other halogens (see, e.g., Chun, J-H and Pike, V. W. *Eur. J. Org. Chem.* (2012) 4541-4547). Iodine, however is a much stronger reducing agent than the other halogens and is therefore more prone to form iodo and diaryliodo radicals.

Provided herein is a method for making a compound of Formula (1):

wherein:
$Ar^2$ is an aryl or heteroaryl ring system; and
I* is a radioactive isotope of iodine;
the method comprising:
(a) reacting a mixture comprising a compound M*I, wherein M is a counter cation, and a compound of Formula (2):

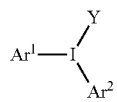

wherein:
$Ar^1$ is an aryl or heteroaryl ring system that is electron-rich as compared to $Ar^2$;
Y is a leaving group; and
$Ar^2$ is as defined above; and
(b) heating the reaction mixture from step (a).

Further provided herein is a method for making a compound of Formula (1)

wherein:
$Ar^2$ is an aryl or heteroaryl ring system; and
*I is a radioactive isotope of iodine;
the method comprising heating a compound of Formula (3):

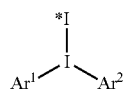

wherein:
$Ar^1$ is an aryl or heteroaryl ring system that is electron-rich as compared to $Ar^2$; and
$Ar^2$ is as defined above.

In any of the above embodiments, the radioactive isotope of iodine can be selected from the group consisting of: $^{123}$I, $^{124}$I, $^{125}$I, $^{131}$I, and mixtures thereof. In some embodiments, the radioactive isotope of iodine is $^{123}$I. In some embodiments, the radioactive isotope of iodine is $^{124}$I. In some embodiments, the radioactive isotope of iodine is $^{125}$I. In some embodiments, the radioactive isotope of iodine is $^{131}$I.

In some embodiments, the specific activity of the radioactive isotope of iodine is at least about 10 mCi/mg. In some embodiments, the specific activity of the radioisotope of iodine is greater than about 1 Ci/mg. In some embodiments, the specific activity is greater than about 10 Ci/mg.

Y can be any suitable leaving group. In some embodiments, Y is a weakly coordinating anion (i.e., an anion that coordinates only weakly with iodine). For example, Y can be the conjugate base of a strong acid, for example, any anion for which the pKa of the conjugate acid (H—Y) is less than about 1. For example, Y can be triflate, mesylate, nonaflate, hexaflate, toluene sulfonate (tosylate), nitrophenyl sulfonate (nosylate), bromophenyl sulfonate (brosylate), perfluoroalkyl sulfonate (e.g., perfluoro $C_{2-10}$ alkyl sulfonate), tetraphenylborate, hexafluorophosphate, trifluoroacetate, perfluoroalkylcarboxylate, tetrafluoroborate, perchlorate, hexafluorostibate, hexachlorostibate, and chloride. In some embodiments, a slightly more basic leaving group such as acetate, triflate, or benzoate may be used.

The counter ion M can be any suitable cation for iodide. The choice of M, is readily within the knowledge of one of ordinary skill in the art. For example, M can be chosen from an alkali metal, alkaline earth metal and transition metal salts such as, for example, calcium, magnesium, potassium, sodium and zinc salts. Metal cations may also be complexed to cryptands or crown ethers to enhance their solubility and to labilize the iodide moiety. M can also include organic salts made from quaternized amines derived from, for example, N,N' dibenzylethylenediamine, chloroprocaine, choline, diethanolamine, ethylenediamine, meglumine (N-methylglucamine) and procaine. In some embodiments, M can be a lithium, sodium, potassium, or cesium with cryptands or crown ethers, a tetrasubstituted ammonium cation, or phosphonium cation. A variety of iodide sources can be used in the preparation of the fluorinated aryl and heteroaryl compounds as provided herein, including but not limited to LiI, NaI, KI, CsI, tetrabutylammonium iodide, and tetramethylammonium iodide. In some embodiments, the iodide salt will be obtained in aqueous solution. In some embodiments, the source radioiodide salt will contain additives, such as sodium hydroxide. In certain instances the choice of iodide source will depend on the functionality present on the compound of Formula (2).

In some embodiments, $Ar^1$—H is more easily oxidized than benzene. For example, $Ar^1$ can be substituted with at least one substituent having a Hammett $\sigma_p$ value of less than zero (see, for example, "A survey of Hammett substituent constants and resonance and field parameters", Corwin. Hansch, A. Leo, R. W. Taft *Chem. Rev.,* 1991, 91 (2), pp 165-195). In some embodiments, the substituent is selected from the group consisting of: —($C_1$-$C_{10}$)alkyl, —($C_1$-$C_{10}$)haloalkyl, ($C_2$-$C_{10}$)alkenyl, ($C_2$-$C_{10}$)alkynyl, —O—($C_1$-$C_{10}$)alkyl, —C(O)—O—($C_1$-$C_{10}$)alkyl, aryl, and heteroaryl.

Examples of $Ar^1$ include:

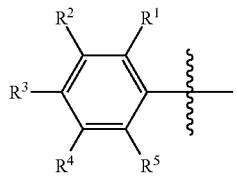

wherein:

$R^1$, $R^2$, $R^3$, $R^4$, and $R^5$ are independently selected from the group consisting of: H, —($C_1$-$C_{10}$)alkyl, —($C_1$-$C_{10}$)haloalkyl, ($C_2$-$C_{10}$)alkenyl, ($C_2$-$C_{10}$)alkynyl, —O—($C_1$-$C_{10}$)alkyl, —C(O)—O—($C_1$-$C_{10}$)alkyl, aryl, and heteroaryl, or two or more of $R^1$, $R^2$, $R^3$, $R^4$, and $R^5$ come together to form a fused aryl or heteroaryl ring system.

In some embodiments, $Ar^1$ can be substituted with a solid support. A "solid support" may be any suitable solid-phase support which is insoluble in any solvents to be used in the process but which can be covalently bound (e.g., directly to $Ar^1$ or via a linker). Examples of suitable solid supports include polymers such as polystyrene (which may be block grafted, for example with polyethylene glycol), polyacrylamide, or polypropylene or glass or silicon coated with such a polymer. The solid support may be in the form of small discrete particles such as beads or pins, or as a coating on the inner surface of a reaction vessel, for example a cartridge or a microfabricated vessel. See, for example, U.S. Patent Application No. 2007/0092441.

In some embodiments, the solid support is covalently bound to $Ar^1$ through the use of a linker. A "linker" can be any suitable organic group which serves to space the $Ar^1$ from the solid support structure so as to maximize reactivity. For example, a linker can include a $C_{1-20}$ alkyl or a $C_{1-20}$ alkoxy, attached to the solid support, for example, via an amide ether or a sulphonamide bond for ease of synthesis. The linker may also be a polyethylene glycol (PEG) linker. Examples of such linkers are well known to those skilled in the art of solid-phase chemistry.

The methods described herein can be used with a variety of aryl and heteroaryl ring systems. As is well understood by one of skill in the art, to carry out efficient nucleophilic substitution of the aryl and heteroaryl ring systems described herein, it is necessary that $Ar^1$ be more easily oxidized (i.e., more electron rich) than $Ar^2$. Within that boundary, however, the $Ar^2$ moiety can be any aryl or heteroaryl ring system in which substitution by a radioisotope of iodine is desired. For example, $Ar^2$ can be a phenylalanine, tyrosine, typtophan, or histidine derivative, and an estradiol derivative.

In some embodiments, $Ar^2$ can be chosen from:

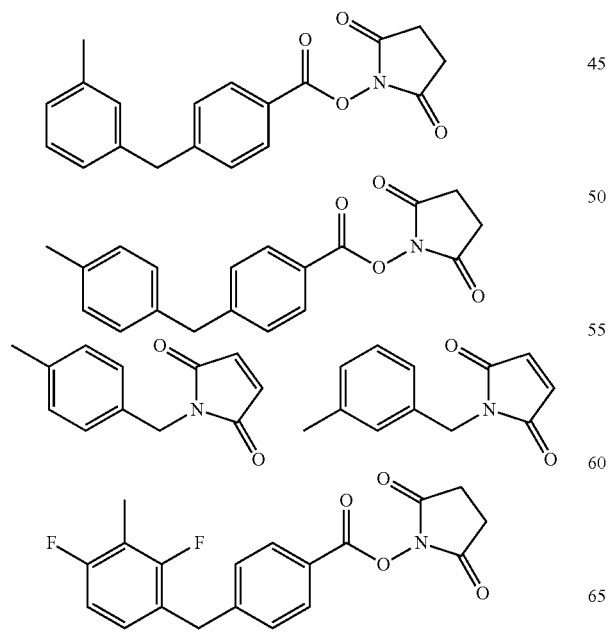

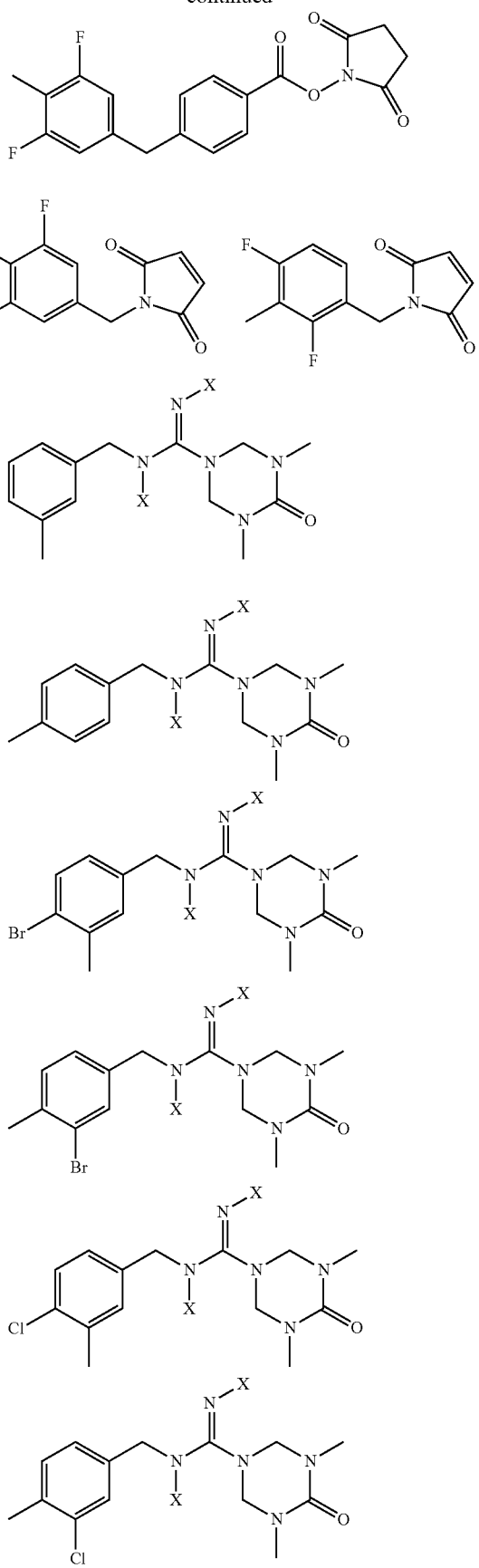

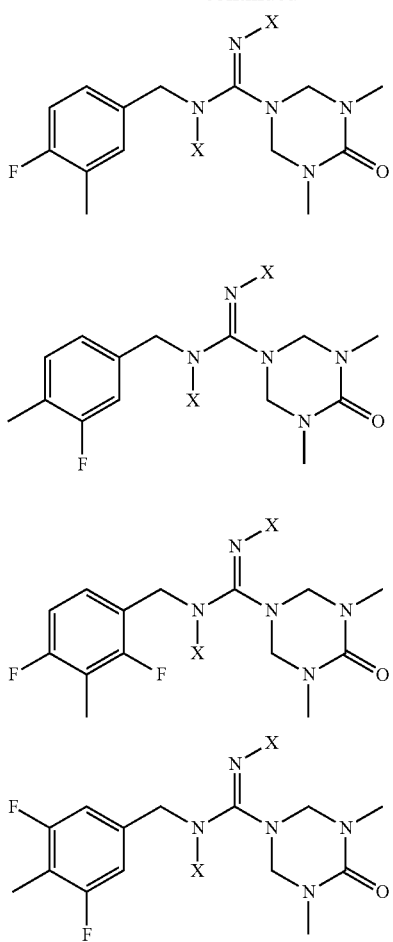

wherein each X is independently a protecting group. For example, Ar² can be selected from the group consisting of:

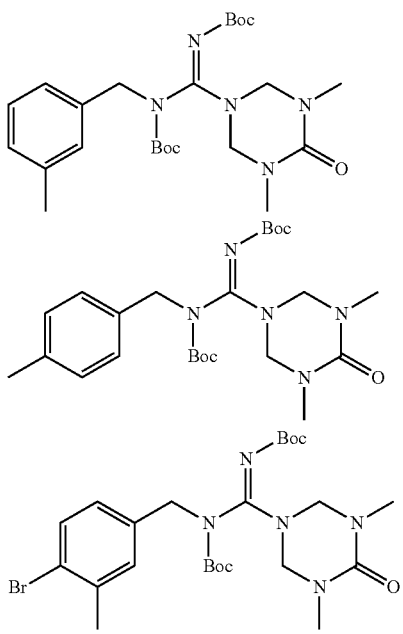

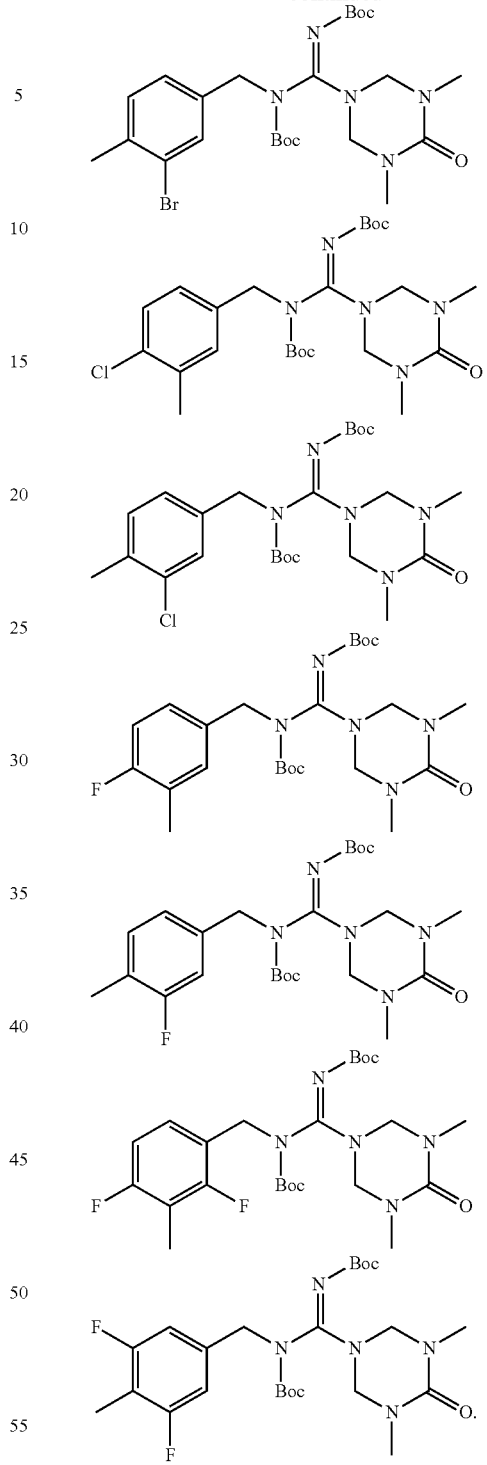

Protecting groups can be a temporary substituent which protects a potentially reactive functional group from undesired chemical transformations. The choice of the particular protecting group employed is well within the skill of one of ordinary skill in the art. A number of considerations can determine the choice of protecting group including, but not limited to, the functional group being protected, other functionality present in the molecule, reaction conditions at each step of the synthetic sequence, other protecting groups present in the molecule, functional group tolerance to conditions required to remove the protecting group, and reaction conditions for the thermal decomposition of the compounds provided herein. The field of protecting group chemistry has been reviewed (Greene, T. W.; Wuts, P. G. M. *Protective Groups in Organic Synthesis,* 2.sup.nd ed.; Wiley: New York, 1991).

For example, protecting groups for amines include, but are not limited to, t-butoxycarbonyl (BOC), benzyloxycarbonyl (Cbz), 2,2,2-trichloroethoxycarbonyl (Troc), 2-(4-trifluoromethylphenylsulfonyl)ethoxycarbonyl (Tsc), 1-adamantyloxycarbonyl (Adoc), 2-adamantylcarbonyl (2-Adoc), 2,4-dimethylpent-3-yloxycarbonyl (Doc), cyclohexyloxycarbonyl (Hoc), 1,1-dimethyl-2,2,2-trichloroethoxycarbonyl (TcBOC), vinyl, 2-chloroethyl, 2-phenylsulfonylethyl, allyl, benzyl, 2-nitrobenzyl, 4-nitrobenzyl, diphenyl-4-pyridylmethyl, N',N'-dimethylhydrazinyl, methoxymethyl, t-butoxymethyl (Bum), benzyloxymethyl (BOM), or 2-tetrahydropyranyl (THP).

Carboxylic acids can be protected as their alkyl, allyl, or benzyl esters, among other groups.

Alcohols can be protected as esters, such as acetyl, benzoyl, or pivaloyl, or as ethers. Examples of ether protecting groups for alcohols include, but are not limited to alkyl, allyl, benzyl, methoxymethyl (MOM), t-butoxymethyl, tetrahydropyranyl (THP), p-methoxybenzyle (PMB), trityl, and methoxyethoxymethyl (MEM).

In some embodiments, the protecting groups are acid labile protecting groups.

In some embodiments, the protecting groups are base labile protecting groups.

In some embodiments, the protecting group are acid labile protecting groups, which can be easily be removed at the end of all synthetic steps under acidic deprotection conditions.

The methods provided herein can be performed in the presence of a solvent (e.g., an aprotic solvent). For example, the reaction can be performed in the presence of a polar solvent, a nonpolar solvent, or a mixture thereof. In some embodiments, the reaction mixture in step (a) further comprises an aprotic solvent as described herein. In some embodiments, the solvent comprises a polar solvent. In some embodiments, the solvent is removed from the reaction mixture prior to step (b). In some embodiments, the reaction mixture in step (b) further comprises a solvent (e.g., an aprotic solvent). In some embodiments, the solvent comprises a nonpolar solvent.

In some embodiments, the method can include reacting in a polar solvent a compound M*I, wherein M is a counter ion, and a compound of Formula (2). The polar solvent can be removed from the reaction mixture following completion of the reaction. The remaining remaining mixture can then be combined with a nonpolar solvent and heated to produce a compound of Formula (1).

In some embodiments, the method can include heating a mixture comprising a nonpolar solvent, a compound M*I, and a compound of Formula (2). For example, the method can include heating a mixture comprising a nonpolar and a polar solvent, a compound M*I, and a compound of Formula (2). In some such embodiments, the nonpolar solvent includes toluene and the polar solvent includes acetonitrile.

In some embodiments, the nonpolar solution of the reaction mixture of M*I and a compound of Formula (2) can be filtered prior to heating. The filtration step can remove any insoluble material (e.g., insoluble salts) that remain in the reaction mixture. In some embodiments, the solvent can be removed from the filtrate prior to heating (i.e., the residue can be heated neat).

In further embodiments, the nonpolar solution of the reaction mixture of M*I and a compound of Formula (2) can be filtered prior to heating, the nonpolar solvent can be removed (e.g., by evaporation), and the heating of the sample can be performed in a different solvent.

In some embodiments, contaminant salts are removed from the solution of the reaction mixture of M*I and a compound of Formula (2) in the polar or nonpolar solution by chromatography. For example, the contaminant salts can be removed by size exclusion, gel filtration, reverse phase, or other chromatographic method prior to heating.

A nonpolar solvent can be any solvent having a dielectric constant of less than about 10. Examples of nonpolar solvents include benzene, toluene, o-xylene, m-xylene, p-xylene, ethyl benzene, carbon tetrachloride, hexane, cyclohexane, fluorobenzene, chlorobenzene, nitrobenzene, and mixtures thereof. In some embodiments, the aprotic solvent comprises toluene.

A polar solvent is a solvent having a dielectric constant greater than about 10. Examples of polar solvents include acetonitrile, acetone, dichloromethane, ethyl acetate, tetrahydrofuran, dimethylformamide, 1,2-difluorobenzene, benzotrifluoride, dimethoxyethane, diglyme, diethyl ether, dibutyl ether, and mixtures thereof. In some embodiments, the aprotic solvent comprises acetonitrile.

In some embodiments, the aprotic solvent is a mixture of a polar and nonpolar solvent. Without being bound by theory, it is believed that the reaction proceeds faster in the presence of a nonpolar solvent while a polar solvent helps to maintain the solubility of the various reactants. In some embodiments, the aprotic solvent is a mixture of a polar and nonpolar solvent wherein the mixture is composed of about 95% polar solvent and about 5% nonpolar solvent, about 90% polar solvent and about 10% nonpolar solvent; about 85% polar solvent and about 15% nonpolar solvent; about 80% polar solvent and about 20% nonpolar solvent; about 75% polar solvent and about 25% nonpolar solvent; about 70% polar solvent and about 30% nonpolar solvent; about 65% polar solvent and about 35% nonpolar solvent; about 60% polar solvent and about 40% nonpolar solvent; about 55% polar solvent and about 45% nonpolar solvent; about 50% polar solvent and about 50% nonpolar solvent; about 45% polar solvent and about 55% nonpolar solvent; about 60% polar solvent and about 40% nonpolar solvent; about 55% polar solvent and about 45% nonpolar solvent; about 45% polar solvent and about 55% nonpolar solvent; about 40% polar solvent and about 60% nonpolar solvent; about 35% polar solvent and about 65% nonpolar solvent; about 30% polar solvent and about 70% nonpolar solvent; about 25% polar solvent and about 75% nonpolar solvent; about 20% polar solvent and about 80% nonpolar solvent; about 15% polar solvent and about 85% nonpolar solvent; about 10% polar solvent and about 90% nonpolar solvent; or about 5% polar solvent and about 95% nonpolar solvent. In some embodiments, the aprotic solvent is a mixture having about 5 to about 20% polar solvent and about 80% to about 95% nonpolar solvent. For example, the mixture can include about 10% polar solvent and about 90% nonpolar solvent. In some embodiments, the polar solvent is acetonitrile and the nonpolar solvent is toluene.

Heating can be accomplished by conventional means (e.g., heating bath, oven, heat gun, hot plate, Bunsen burner, heating mantle, and the like), by the use of a microwave, or by flash pyrolysis. Typically, the reaction mixture is heated at a temperature ranging from about 25° C. to about 250° C. (e.g., between about 80° C. to about 200° C., 100° C. to about 200° C., about 120° C. to about 170° C., about 120° C. to about 160° C., about 120° C. to about 150° C., and about 130° C. to about 150° C.). In some embodiments, the reaction mixture is heated to about 140° C. Heating can occur for any time necessary to complete the reaction. For example, heating can occur for from about 1 second to about 12 hours (e.g., about 2 seconds, about 5 seconds, about 10 seconds, about 30 seconds, about 1 minute, about 90 seconds, about 2 minutes, about 3 minutes, about 5 minutes, about 8 minutes, about 10 minutes, about 12 minutes, about 15 minutes, about 20 minutes, about 25 minutes, about 30 minutes, about 1 hour, about 2 hours, about 3 hours, about 4 hours, about 6 hours, about 8 hours, about 10 hours, and about 12 hours). In some embodiments, heating can occur for from about 1 second to about 2 hours.

In some embodiments, a compound of Formula (2) is selected from the group consisting of:

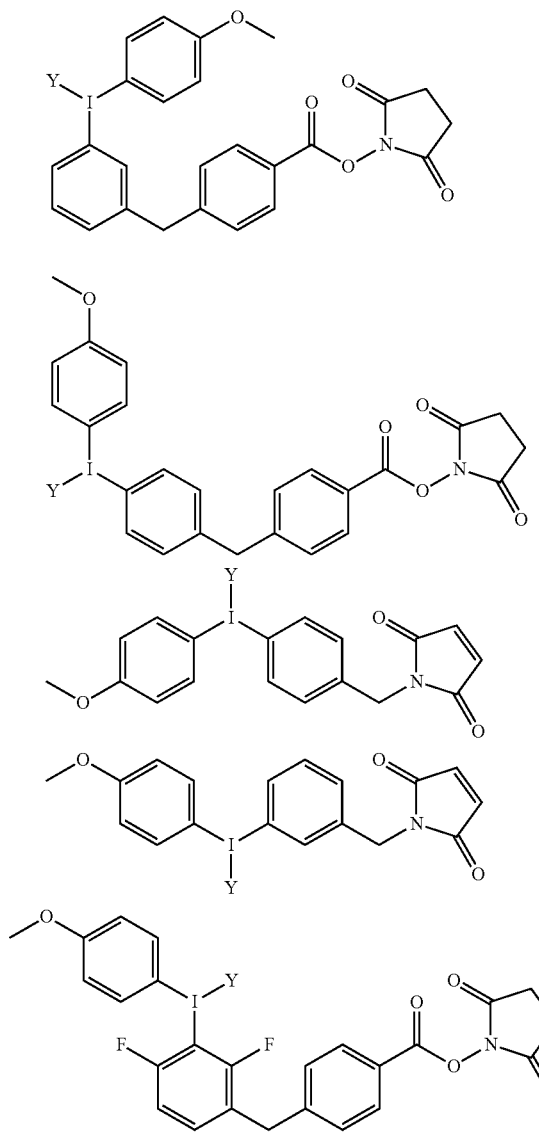

-continued

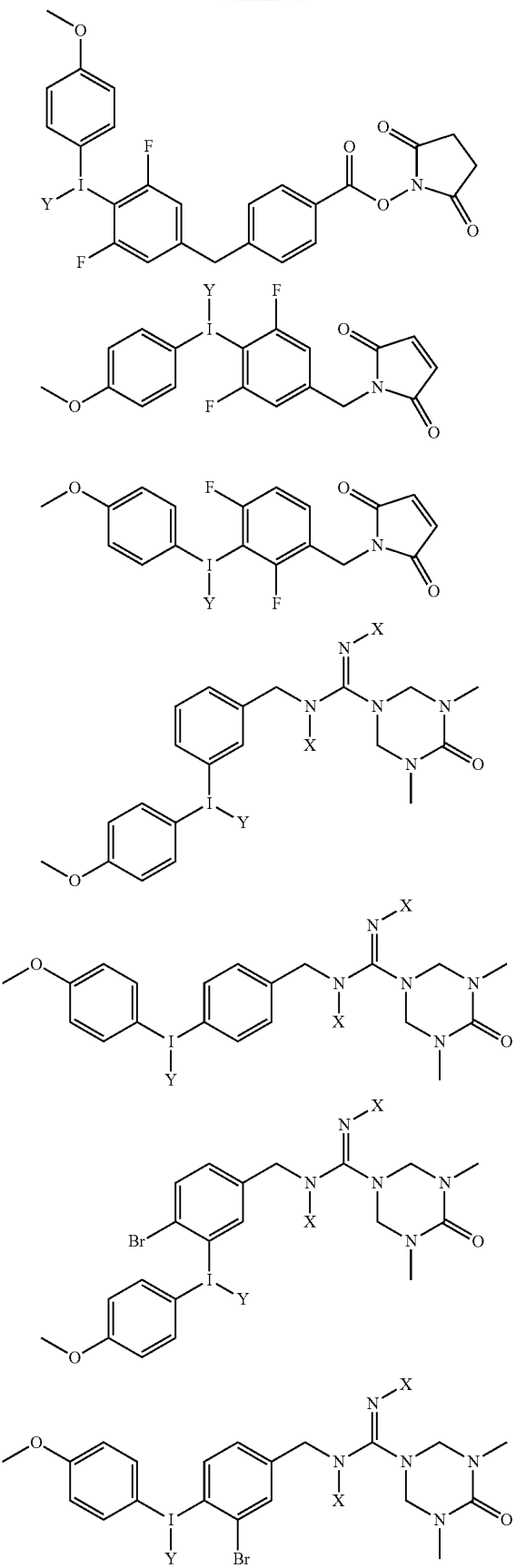

-continued
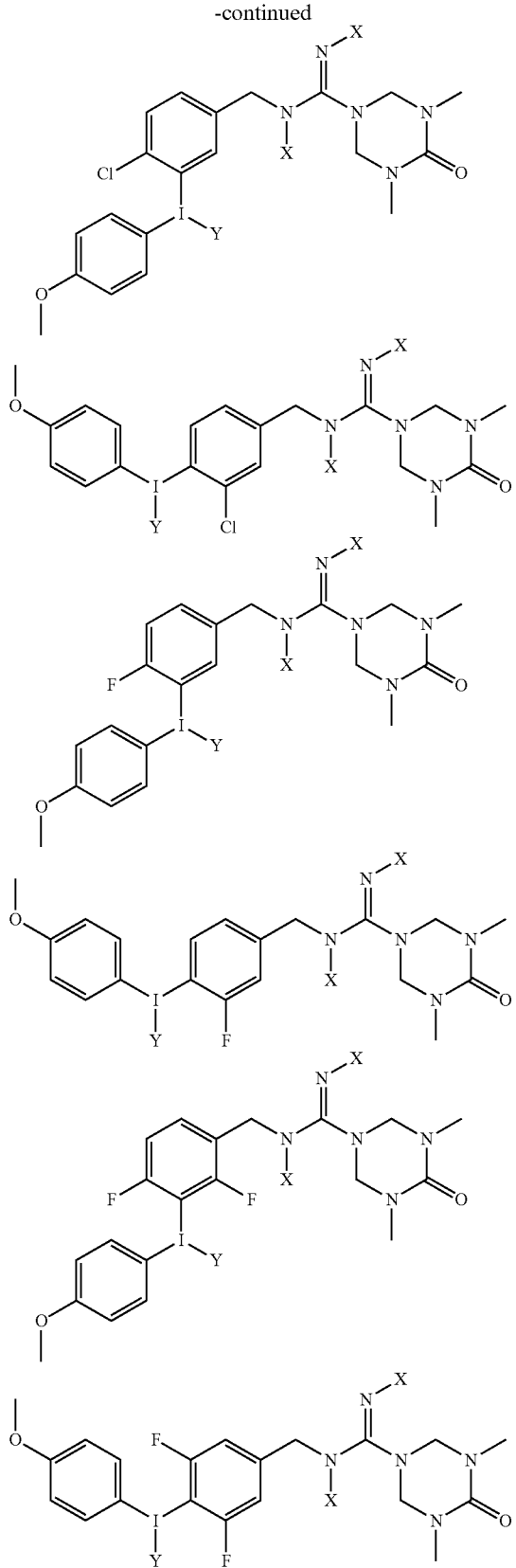
wherein each Y is independently a leaving group as defined above; and
each X is independently a protecting group.
For example, a compound of Formula (2) can be selected from the group consisting of:
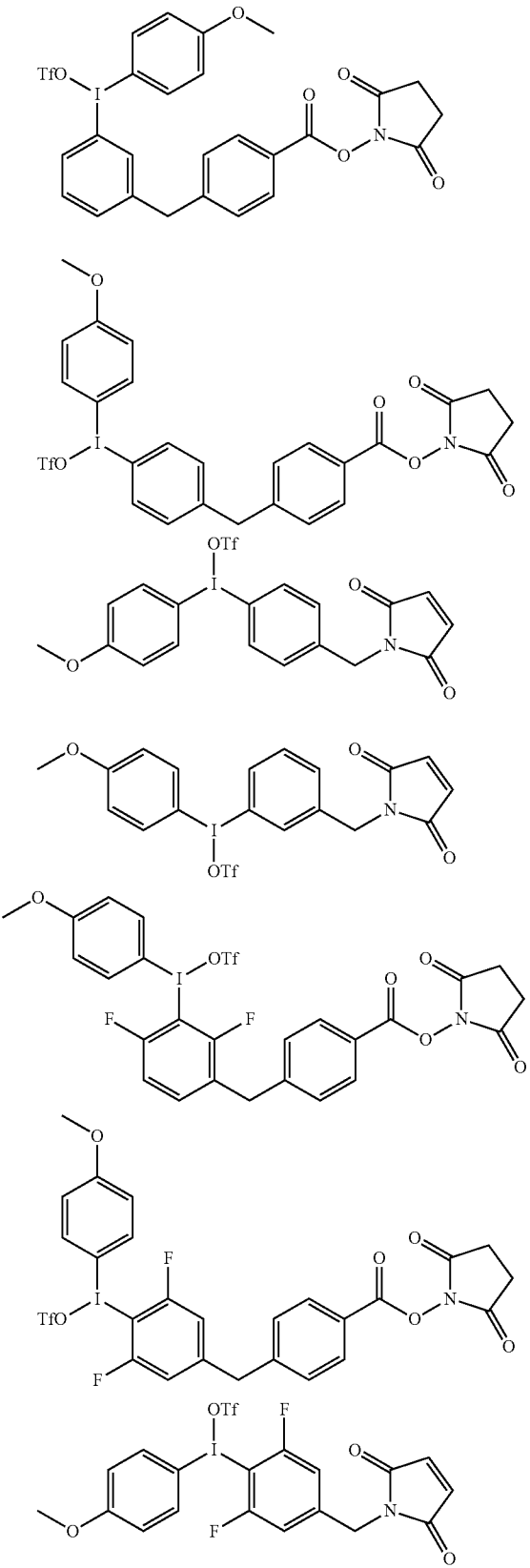

-continued
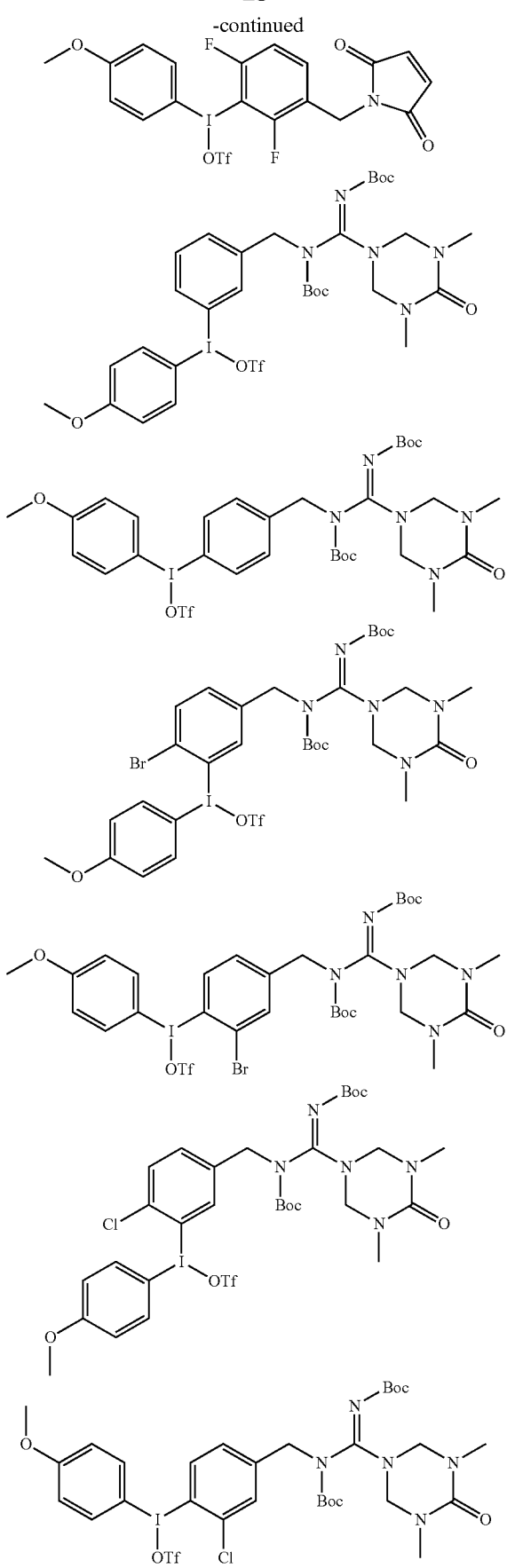
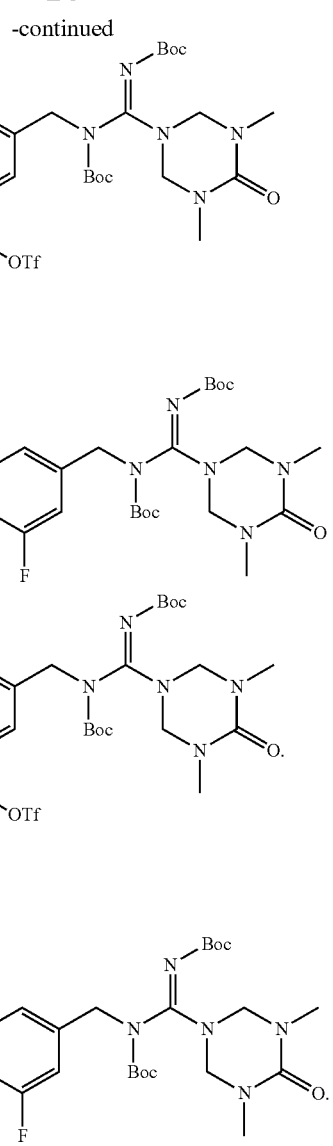
In some embodiments, a compound of Formula (1) is selected from the group consisting of:
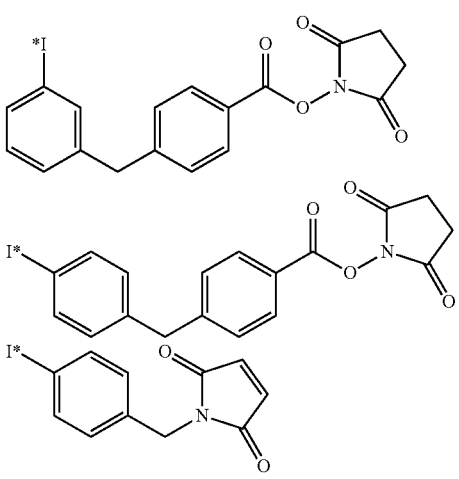

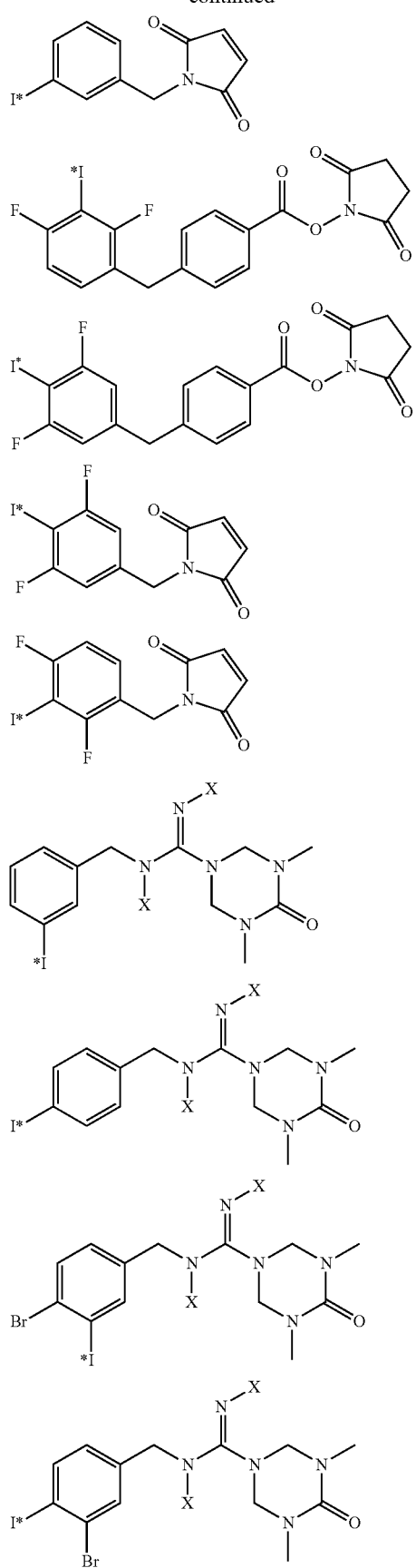
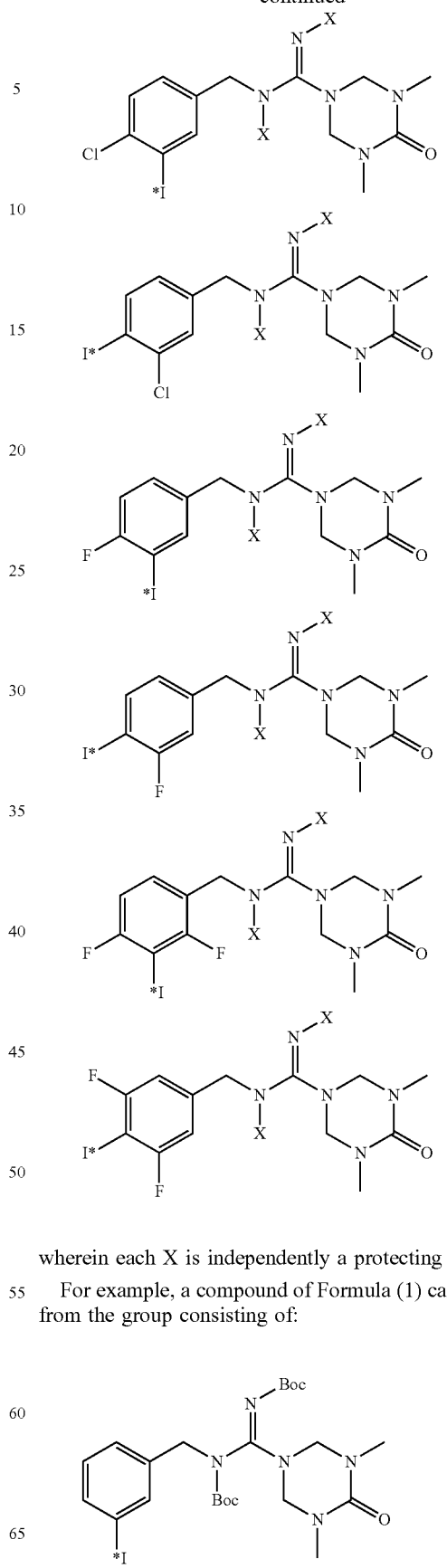
wherein each X is independently a protecting group.
For example, a compound of Formula (1) can be selected from the group consisting of:
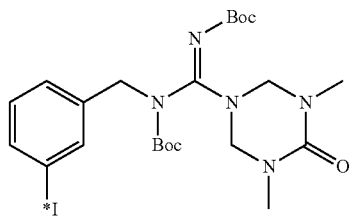

-continued
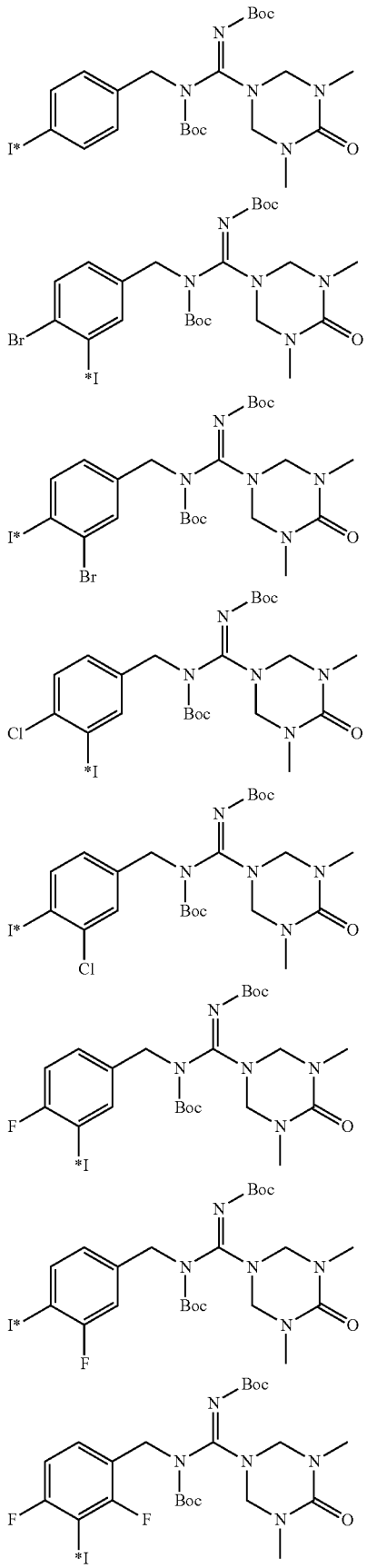
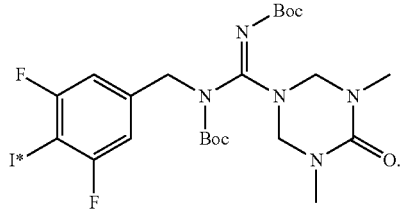
Non-limiting examples of a compound of Formula (3) include:
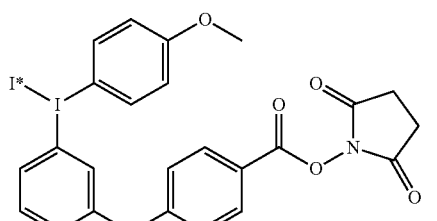
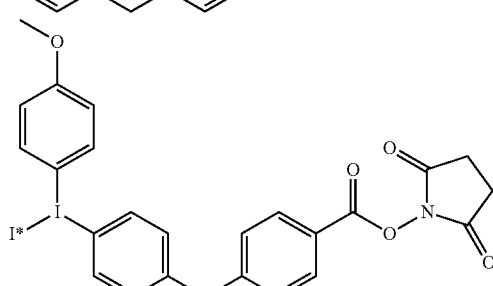
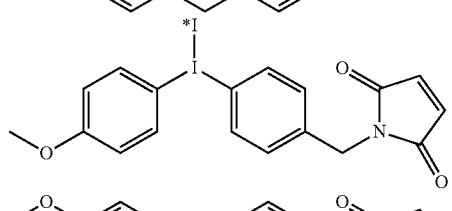
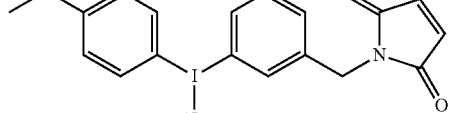
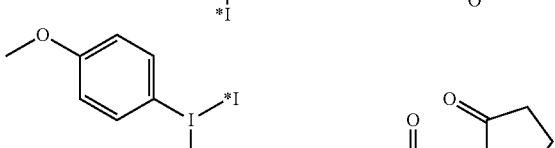
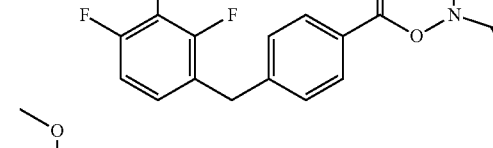
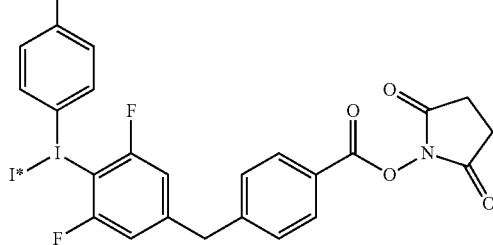

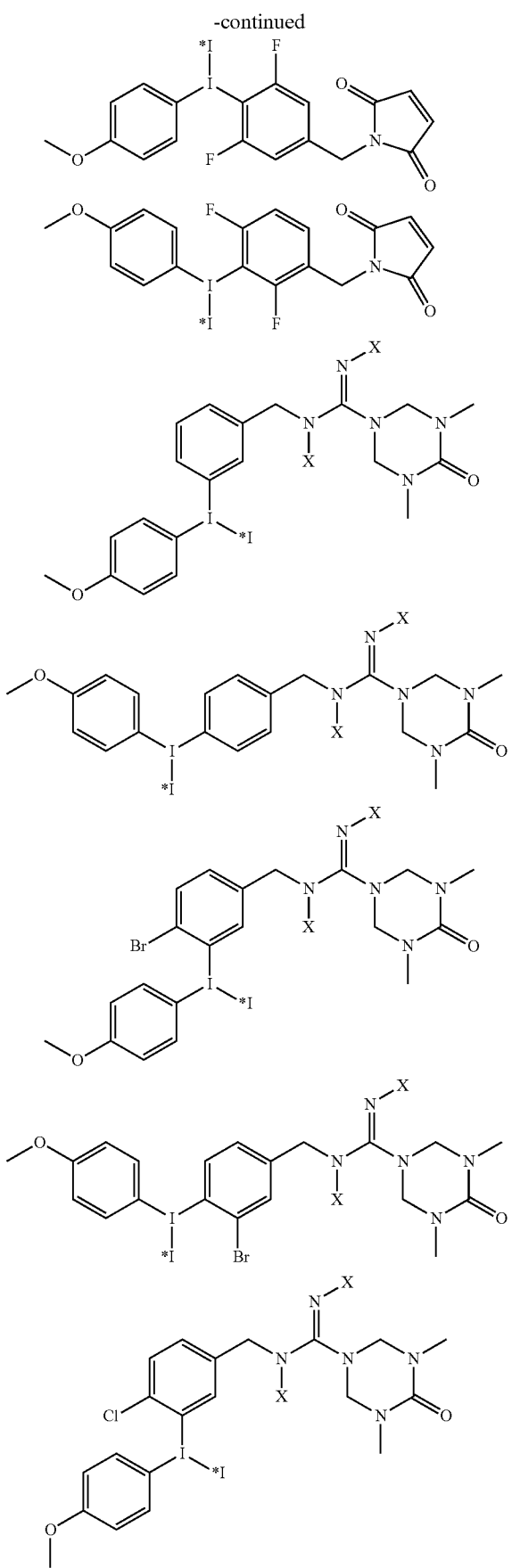
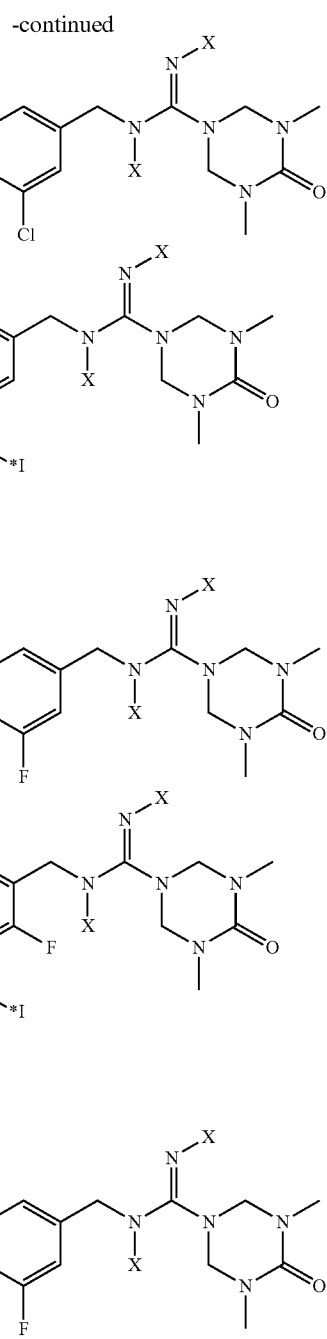
wherein each Y is independently a leaving group as defined above; and
each X is independently a protecting group.
In some embodiments, a compound of Formula (3) is selected from the group consisting of:
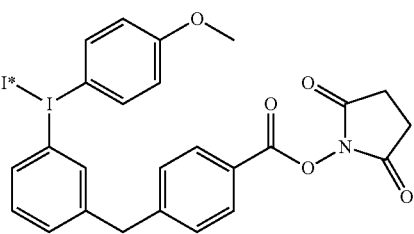

31
-continued
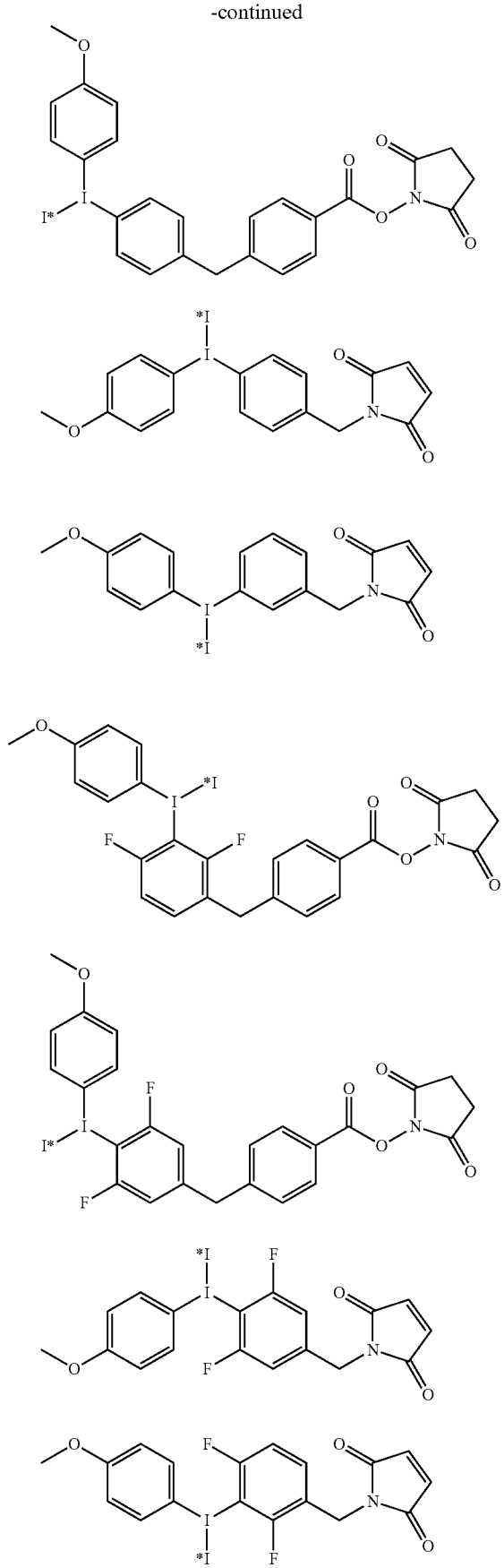
32
-continued
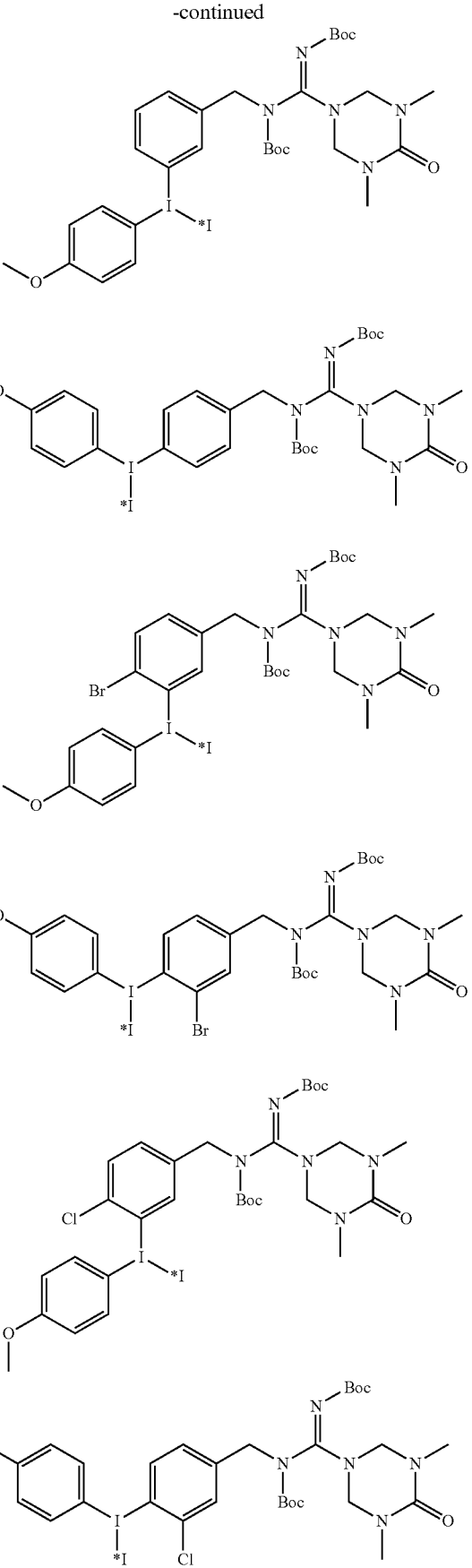

-continued

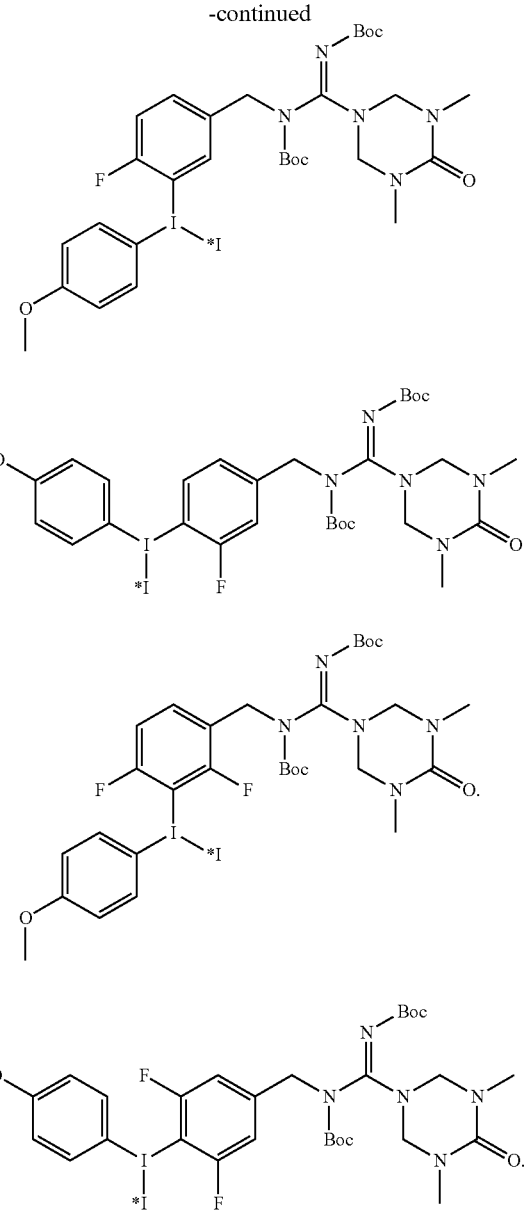

Compounds

Diaryliodonium compounds, for example, compounds of Formulas (2) and (3), are further provided herein. The diaryliodonium compounds of Formulas (2) and (3) can be prepared from commercially available starting materials using various methods known to those of ordinary skill in the art. The method used for synthesizing the compounds will depend on the electronics and functionality present in of $Ar^2$. Potentially reactive functional groups present in $Ar^2$ can be masked using a protecting group prior to the synthesis of the diaryliodonium compound. The particular method employed for preparing the diaryliodonium compounds will be readily apparent to a person of ordinary skill in the art. For example, the compounds can be made using the following generic reactions as shown in Scheme 2.

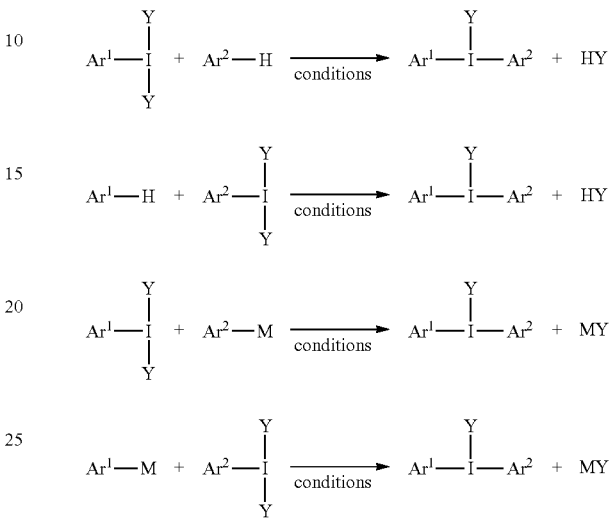

Scheme 2.

For compounds that bear sensitive functionality on the accepting group, organometallic reagents that feature more covalent (more stable) C-M bonds can be used. For example, organometallic compounds including tin, boron, and zinc. If there is no functional group incompatibility, more basic organometallic reagents (organolithium, Grignard, etc.) can be used to prepare the diaryliodonium salts.

Persons skilled in the art will be aware of variations of, and alternatives to, the processes described which allow the compounds defined herein to be obtained.

It will also be appreciated by persons skilled in the art that, within certain of the processes described, the order of the synthetic steps employed may be varied and will depend inter alia on factors such as the nature of other functional groups present in a particular substrate, the availability of key intermediates, and the protecting group strategy (if any) to be adopted. Clearly, such factors will also influence the choice of reagent for use in the said synthetic steps.

The skilled person will appreciate that the diaryliodonium compounds described could be made by methods other than those herein described, by adaptation of the methods herein described and/or adaptation of methods known in the art, for example US 2007/0092441, or using standard textbooks such as "Comprehensive Organic Transformations—A Guide to Functional Group Transformations", R C Larock, Wiley-VCH (1999 or later editions) and Science of Synthesis, Volume 31a, 2007 (Houben-Weyl, Thieme)

As exemplified in the examples below, certain diaryliodonium iodides can be prepared as shown in Scheme 1.

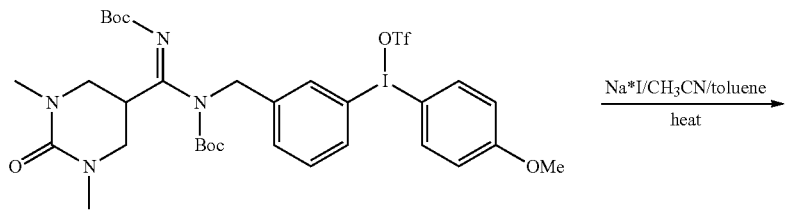

-continued

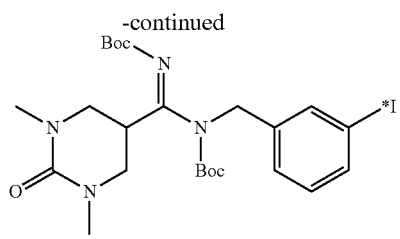

It is to be understood that the synthetic transformation methods mentioned herein are exemplary only and they may be carried out in various different sequences in order that the desired compounds can be efficiently assembled. The skilled chemist will exercise his judgment and skill as to the most efficient sequence of reactions for synthesis of a given target compound.

Kit

Also provided herein are kits. Typically, a kit is used to prepare a compound of Formula (1) as provided herein prior to administration. In some embodiments, the kit comprises a compound of Formula (2). In some embodiments, the kit can further include a purified solvent (e.g., a substantially waterless solvent). In some embodiments, the kit can further include one to four chromatography cartridges (e.g., to purify the final radioiodinated compound prior to administration). In some embodiments, the kit can further include an acidic reagent (e.g., to remove any protecting groups incorporated into the compound of Formula (2)). In certain embodiments, a kit can include one or more delivery systems, e.g., for delivering or administering a compound of Formula (I) as provided herein, and directions for use of the kit (e.g., instructions for preparing the compound of Formula (1)).

EXAMPLES

The invention is further described in the following examples, which do not limit the scope of the invention described in the claims.

Example 1: Preparation of N-(3-iodobenzyl)maleimide

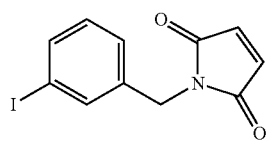 [SMILES: O=C1C=CC(=O)N1Cc1cccc(I)c1]

Diisopropyl azodicarboxylate (DIAD) (12 mmol, 2.43 g, 2.40 mL, 1.2 eq.) was added over the course of one hour to a solution of 3-iodobenzyl alcohol (10 mmol, 2.34 g, 1.0 eq.), PPh$_3$ (11 mmol, 2.88 g, 1.1 eq.), and maleimide (11 mmol, 1.07 g, 1.1 eq.) in 100 mL of THF. After the resulting yellow solution was stirred overnight, the solvent was removed and the residue was purified by column chromatography on silica gel (hexanes:ethyl acetate=1:5, R$_f$=0.3) and washed with hexane to obtain 1.79 g (57%) of product as a white solid. $^1$H NMR (CD$_3$CN, 400 MHz): δ 7.64 (d, J=1.6 Hz, 1H), 7.63 (d, J=9.6 Hz, 1H), 7.27 (d, J=7.6 Hz, 1H), 7.09 (t, J=7.6 Hz, 1H), 6.78 (s, 6H), 4.56 (s, 2H).

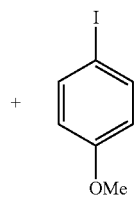

Example 2: Preparation of [3-((2,5-dioxo-2,5-dihydro-1H-pyrrol-1-yl)methyl)phenyl]-(4'-methoxyphenyl)iodonium triflate

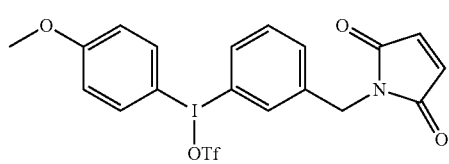 [SMILES: COc1ccc(I(OS(=O)(=O)C(F)(F)F)c2cccc(CN3C(=O)C=CC3=O)c2)cc1]

In a N$_2$ charged glovebox, a solution of TMSOAc (10.4 mmol, 1.37 g, 2.6 eq.) in 50 mL of dry CH$_3$CN was added dropwise to a solution of Selectfluor™ (5.2 mmol, 1.84 g, 1.3 eq.) in 50 mL of dry CH$_3$CN. The resulting colorless mixture was then added dropwise to a solution of N-(3-iodobenzyl)maleimide (4 mmol, 1.25 g, 1.0 eq.) in dry CH$_3$CN (150 mL). After the resulting solution was stirred at room temperature for one day, potassium 4-methoxyphenyltrifluoroborate (856 mg, 4 mmol, 1.0 equiv.) was added. Immediately thereafter, a solution of TMSOTf (764 mg, 3.4 mmol, 0.8 eq.) in 50.0 mL of dry CH$_3$CN was added in a dropwise fashion, and the mixture was allowed to stand at room temperature for 30 min. The acetonitrile was removed under reduced pressure. Deionized water (200 mL) was added to the remaining solid and the mixture was extracted (3×50 mL) with CH$_2$Cl$_2$. The combined organic layers were washed with water (50 mL) and the obtained water layer was extracted (50 mL×2) with CH$_2$CH$_2$ again. The combined organic extracts were dried over sodium sulfate, filtered, and the solvent was removed by rotary evaporation. This compound was dissolved in 1 mL acetonitrile/water (9:1 by volume) solution and slowly passed down an Amberlite IRA-400 ion exchange column (triflate counterion). After removal of the solvents under reduced pressure, the purified iodonium triflate product (1.06 g, 47%) was obtained by washing the colorless residue with EtOAc to remove any organic impurities. $^1$H NMR (CD$_3$CN, 400 MHz): δ 7.98 (d, J=8.4 Hz, 2H), 7.90 (d, J=8.4 Hz, 2H), 7.86 (s, 1H), 7.58 (d, J=7.2 Hz, 1H), 7.47 (t, J=8.0 Hz, 1H), 7.07 (d, J=8.4 Hz, 2H), 6.83 (s, 2H), 4.64 (s, 2H), 3.85 (s, 3H); $^{19}$F NMR (CD$_3$CN, 376 MHz): δ −79.3 (s, 3F).

Example 3: Preparation of [4-((2,5-dioxo-2,5-dihydro-1H-pyrrol-1-yl)methyl)phenyl]-(4'-methoxyphenyl)iodonium triflate

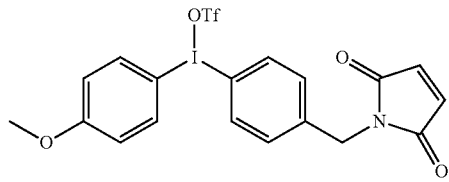 [SMILES: COc1ccc(I(OS(=O)(=O)C(F)(F)F)c2ccc(CN3C(=O)C=CC3=O)cc2)cc1]

This compound was prepared from N-(4-iodobenzyl)maleimide using the same procedure that is described in example 2. A (3 mmol scale reaction yielded 910 mg of product, (53%). $^1$H NMR (CD$_3$CN, 400 MHz): δ 7.99 (d, J=9.2 Hz, 2H), 7.97 (d, J=8.8 Hz, 2H), 7.40 (d, J=8.4 Hz, 2H), 7.05 (d, J=9.2 Hz, 2H), 6.80 (s, 2H), 4.67 (s, 2H), 3.84 (s, 3H); $^{19}$F NMR (CD$_3$CN, 376 MHz): δ −79.3 (s, 3F).

Example 4: Preparation of 4-(4-iodobenzyl)benzoic acid

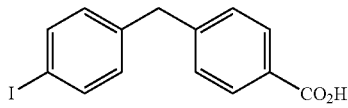

In a 500 mL round bottom flask that was shielded from light with aluminum foil, a stirred solution of 4-benzylbenzoic acid (1.06 g, 5 mmol, 1.0 eq.), NIS (1.24 g, 5.5 mmol, 1.1 eq.) and Yb(OTf)$_3$ (310 mg, 0.50 mmol, 0.1 eq.) in CH$_3$CN (100 mL) was heated to 75-80° C. for 12 hours. After 12 h, a supplementary portion of NIS (0.56 g, 2.5 mmol, 0.5 eq.) was added to drive the reaction to completion. After an additional hour, the solvent was removed by rotary evaporation, and the residue was partitioned between water and ethyl acetate. The mixture was extracted (3×50 mL) with ethyl acetate and the combined organic extracts were washed with water, dried over MgSO$_4$, and filtered. The solvent was removed by rotary evaporation, and the residue was purified by flash chromatography on silica gel (hexanes:ethyl acetate=1:1, Rf=0.2) to give 4-(4-iodobenzyl) benzoic acid as a white solid (1.28 g, 76%). $^1$H NMR (CD$_3$CN, 400 MHz): δ 7.91 (d, J=8.0 Hz, 2H), 7.65 (d, J=8.4 Hz, 2H), 7.31 (d, J=8.4 Hz, 2H), 7.03 (d, J=8.4 Hz, 2H), 3.99 (s, 2H).

Example 5: Preparation of 2,5-dioxopyrrolidin-1-yl 4-(4-iodobenzyl)benzoate

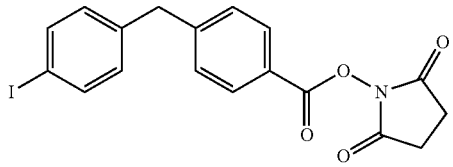 [SMILES: O=C(ON1C(=O)CCC1=O)c1ccc(Cc2ccc(I)cc2)cc1]

4-(4-Iodobenzyl)benzoic acid (3.8 mmol, 1.28 g, 1.0 eq.) and N-hydroxysuccinimide (5.7 mmol, 0.66 g, 1.5 eq) were dissolved in anhydrous CH$_2$Cl$_2$ (20 mL). The mixture was cooled to 0° C. before N,N'-dicyclohexylcarbodiimide (DCC, 5.7 mmol, 1.18 g, 1.5 eq) dissolved in 10 mL CH$_2$Cl$_2$ was added in a dropwise fashion. The mixture was stirred for 12 hours at room temperature and filtered to remove precipitated N,N'-dicyclohexylurea. The residue was washed with additional CH$_2$Cl$_2$, and the combined filtrate was evaporated in vacuo. The residue was purified by column chromatography (hexanes:ethyl acetate=1:5, Rf=0.6). Recrystallization with isopropanol or toluene/hexane afforded the title compound as a colorless solid (0.60 g, 36%). Recrystallization with isopropanol or toluene/hexane afforded the title compound as a colorless solid. $^1$H NMR (CD$_3$CN, 400 MHz): δ 8.04 (d, J=8.4 Hz, 2H), 7.67 (d, J=8.4 Hz, 2H), 7.42 (d, J=8.4 Hz, 2H), 7.04 (d, J=8.4 Hz, 2H), 4.05 (s, 2H), 2.83 (s, 4H).

Example 6: Preparation of [4-(4-(((2,5-dioxopyrrolidin-1-yl)oxy)carbonyl)benzyl)phenyl]-]-(4'-methoxyphenyl)iodonium triflate

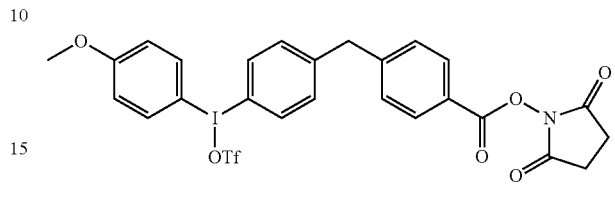

In a N$_2$ charged glovebox, a solution of TMSOAc (3.90 mmol, 516 mg, 2.6 eq.) in 20 mL of dry CH$_3$CN was added dropwise to a solution of Selectfluor™ (1.95 mmol, 691 mg, 1.3 eq.) in 20 mL of dry CH$_3$CN. The resulting colorless mixture was then added slowly (dropwise) to a solution of 2,5-dioxopyrrolidin-1-yl 4-(4-iodobenzyl)benzoate (1.5 mmol, 653 mg, 1.0 eq.) in 40 mL of dry CH$_3$CN. The mixture was stirred at room temperature for 2 days before potassium 4-methoxyphenyltrifluoroborate (320 mg, 1.5 mmol, 1.0 equiv.) was added. Immediately thereafter, a solution of TMSOTf (267 mg, 1.2 mmol, 0.8 eq.) in 20.0 mL of dry CH$_3$CN was added slowly (dropwise), and the mixture was allowed to stand at room temperature for 30 minutes. The acetonitrile was removed by rotary evaporation, 100 mL of deionized water was added, and the mixture was extracted (3×30 mL) with CH$_2$Cl$_2$. The combined organic extracts were washed with water (50 mL) and the aqueous layer was extracted (2×50 mL) with CH$_2$Cl$_2$ again. The combined organic extracts were dried over sodium sulfate, filtered, and concentrated in vacuo. The residue was washed with methy t-butyl ether (MTBE). This compound was dissolved in 1 mL acetonitrile/water (9:1 by volume) solution and slowly passed down an Amberlite IRA-400 ion exchange column (triflate counterion). After removal of the solvents under reduced pressure, the purified iodonium triflate product was obtained by washing the colorless residue with pentane to remove any organic impurities (540 mg, 52%). $^1$H NMR (CD$_3$CN, 400 MHz): δ 8.05 (d, J=8.0 Hz, 2H), 7.99 (d, J=9.2 Hz, 2H), 7.95 (d, J=8.4 Hz, 2H), 7.42 (d, J=8.4 Hz, 2H), 7.38 (d, J=8.4 Hz, 2H), 7.05 (d, J=9.2 Hz, 2H), 4.16 (s, 2H), 3.83 (s, 3H), 2.84 (s, 4H); $^{19}$F NMR (CD$_3$CN, 376 MHz): δ −79.3 (s, 3F).

Example 7: Preparation of 5-Benzyl-1,3-dimethyl-[1,3,5]triazinan-2-one

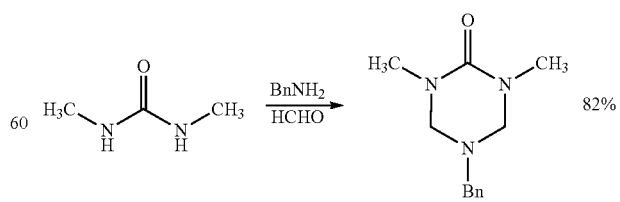

Benzylamine (5 mL, 45.8 mmol), formaldehyde (37% w/w solution, 7.5 mL, 91.6 mmol), and N,N'-dimethylurea (4.03 g, 45.8 mmol) were combined in a reaction flask equipped with a reflux condenser and heated to 100° C. under an nitrogen atmosphere for 16 h. After it was cooled to room temperature, the reaction mixture was quenched with water (50 mL) and extracted with CH$_2$Cl$_2$ (50 mL×2). The combined organic layers were washed with brine, dried over anhydrous Na$_2$SO$_4$, filtered, and concentrated. The residue was purified by flash chromatography (silica gel, EtOH as eluent) to give 5-benzyl-1,3-dimethyl-[1,3,5]triazinan-2-one (8.28 g, 82% yield), isolated as a colorless solid. $^1$H NMR (400 MHz, CDCl$_3$) δ 7.40-7.27 (m, 5H), 4.12 (s, 4H), 3.93 (s, 2H), 2.86 (s, 6H).

Example 8: Preparation of 1,3-Dimethyl-[1,3,5]triazinan-2-one

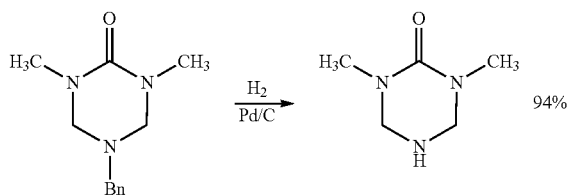

5-Benzyl-1,3-dimethyl-[1,3,5]triazinan-2-one (3.25 g, 14.8 mmol) was dissolved in EtOH (90 mL). To this solution was added Pd/C (10%) (500 mg), and the resulting mixture was heated to 65° C. under H$_2$ (750 psi) for 7 days. After the mixture was allowed to cool to room temperature, the suspension was filtered through Celite, and the eluent was concentrated by rotary evaporation to give 1,3-dimethyl-[1,3,5]triazinan-2-one (1.80 g, 94% yield), isolated as a colorless solid. $^1$H NMR (400 MHz, CDCl$_3$) δ 4.14 (s, 4H), 2.84 (s, 6H), 2.52 (brs, 1H).

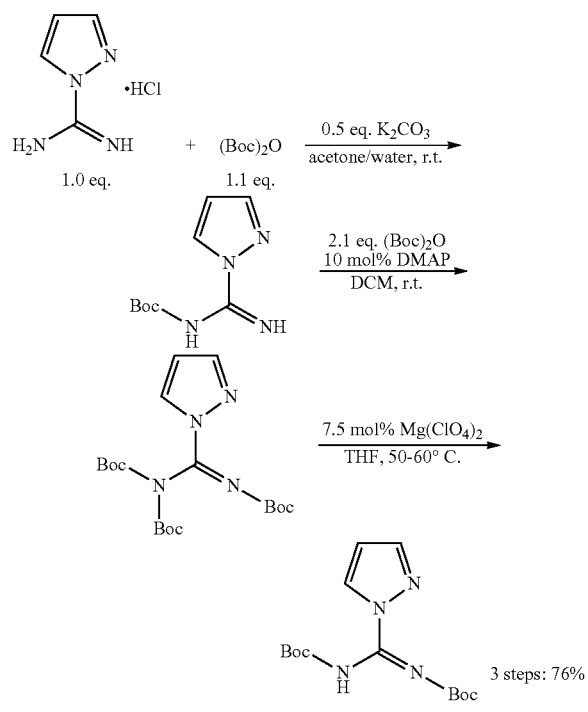

Example 9: Preparation of tert-butyl (imino(1H-pyrazol-1-yl)methyl)carbamates

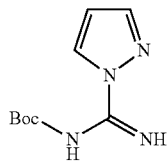 [SMILES: CC(C)(C)OC(=O)NC(=N)n1cccn1]

To a solution of di-tert-butyldicarbonate (13.4 g, 61.5 mmol) in acetone (45 mL) were added 1H-pyrazole-1-carboxamidine hydrochloride (9.0 g, 61.5 mmol, 1.0 equiv.) and 9.0 mL of water. K$_2$CO$_3$ (4.24 g, 30.6 mmol, 0.5 equiv.) in H$_2$O (12.0 mL) was added dropwise for 30 min at room temperature. After 2 h, another portion of di-tert-butyldicarbonate (1.35 g, 6 mmol, 0.1 equiv.) was added and the solution was stirred overnight. The acetone was removed under reduced pressure and the resulting white solid was dissolved in 30.0 mL of water, and allowed to stir at 0° C. for 30 min. The precipitated tert-butyl (imino(1H-pyrazol-1-yl)methyl)carbamate was collected by filtration, washed with water, washed with hexane, and dried in vacuo to provide the title compound as a colorless solid (11.37 g, 88% yield). $^1$H NMR (CDCl$_3$, 400 MHz): δ 9.06 (brs, 1H), 8.45 (d, J=3.2 Hz, 1H), 7.67 (d, J=0.8 Hz, 1H), 7.59 (brs, 1H), 6.39 (dd, J=2.8, 1.6 Hz, 1H), 1.54 (s, 9H).

Example 10: Preparation of tert-butyl tert-butoxycarbonyl(((tert-butoxycarbonyl)imino)(1H-pyrazol-1-yl)methyl)carbamate

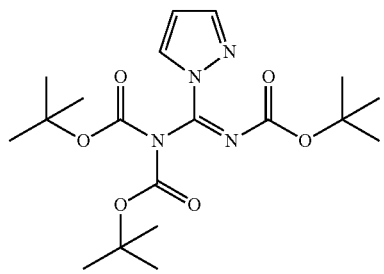 [SMILES: CC(C)(C)OC(=O)/N=C(/N(C(=O)OC(C)(C)C)C(=O)OC(C)(C)C)n1cccn1]

4-(Dimethylamino)pyridine (660 mg, 5.41 mmol) was added to a solution of tert-butyl(((tert-butoxycarbonyl)imino)(1H-pyrazol-1-yl)methyl)carbamate (11.37 g, 54.1 mmol, 1.0 equiv.) in dichloromethane (60 mL). Di-tert-butyldicarbonate (23.61 g, 108.2 mmol, 2.0 equiv.) in THF (40.0 mL) was slowly added over the course of 8 h using a syringe pump. The solution was stirred overnight at room temperature, before the solvents were removed in vacuo. The resulting colorless solid was stirred in dilute acetic acid solution (0.52 g, 8.66 mmol, acetic acid in 60 mL water). The precipitated tert-butyl tert-butoxycarbonyl(((tert-butoxycarbonyl)imino)(1H-pyrazol-1-yl)methyl)carbamate was collected, washed with water, hexane, and dried in vacuo to yield a colorless solide (20.21 g, 91% yield). $^1$H NMR (CDCl$_3$, 400 MHz): δ 8.20 (d, J=2.4 Hz, 1H), 7.69 (d, J=0.8 Hz, 1H), 6.45 (dd, J=2.8, 1.6 Hz, 1H), 1.54 (s, 9H), 1.39 (s, 18H).

Example 11: Preparation of tert-butyl (((tert-butoxycarbonyl)imino)(1H-pyrazol-1-yl)methyl)carbamate

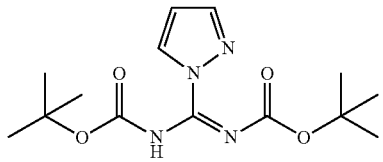 [SMILES: CC(C)(C)OC(=O)/N=C(/NC(=O)OC(C)(C)C)n1cccn1]

The compound prepared in example 10 (tert-butyl tert-butoxycarbonyl(((tert-butoxycarbonyl)imino)(1H-pyrazol-1-yl)methyl)carbamate) (20.21 g, 49.2 mmol, 1.0 equiv.), Mg(ClO$_4$)$_2$ (823 mg, 3.69 mmol, 0.075 equiv.) and THF (70 mL) were added to an over-dried, round bottomed flask, and the mixture was stirred at 50-60° C. for 5 hours. After completion of the reaction (as monitored by TLC), the solvent was evaporated in vacuo and the residue was purified on silica gel chromatography (EtOAc/hexane, 1:10) to afford tert-butyl (((tert-butoxycarbonyl)imino)(1H-pyrazol-1-yl)methyl)carbamates, isolated as a colorless solid (14.58 g, 95% yield). $^1$H NMR (CDCl$_3$, 400 MHz): δ 8.94 (brs, 1H), 8.31 (d, J=2.8 Hz, 1H), 7.63 (d, J=1.6 Hz, 1H), 6.42 (dd, J=2.8, 1.6 Hz, 1H), 1.56 (s, 9H), 1.50 (s, 9H).

Example 12: Preparation of tert-butyl (((tert-butoxycarbonyl)imino)(3,5-dimethyl-4-oxo-1,3,5-triazinan-1-yl)methyl)carbamate

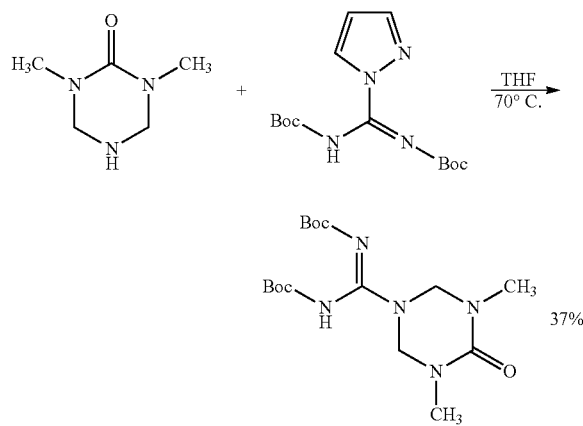

The compound prepared in example 11 (tert-butyl (((tert-butoxycarbonyl)imino)(1H-pyrazol-1-yl)methyl)carbamate), (1.15 g, 3.7 mmol, 1.0 equiv.) and 1,3-dimethyl-[1,3,5]triazinan-2-one (0.57 g, 4.4 mmol, 1.2 equiv.) were dissolved in dry THF (15 mL) under argon in an over-dried flask. This solution was heated at 70° C. for 22 h. The mixture was allowed to cool to room temperature, the solvent was removed in vacuo, and the residue was purified by flash chromatography (silica gel, EtOAc as eluent) to give the product as a colorless solid (0.51 g, 37% yield). $^1$H NMR (400 MHz, CDCl$_3$) δ 10.5 (brs, 1H), 4.70 (s, 4H), 2.92 (s, 6H), 1.51 (s, 9H), 1.50 (s, 9H).

Example 13: Preparation of tert-butyl (((tert-butoxycarbonyl)imino)(3,5-dimethyl-4-oxo-1,3,5-triazinan-1-yl)methyl)(3-iodobenzyl)carbamate

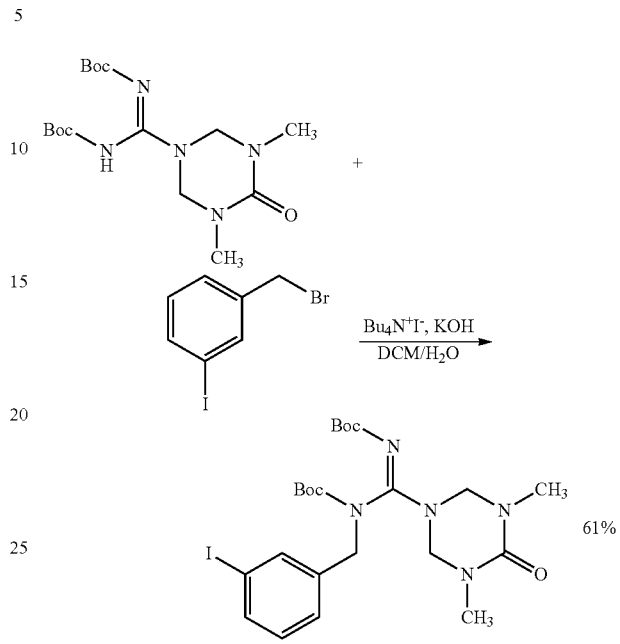

A biphasic solution of tert-butyl (((tert-butoxycarbonyl)imino)(3,5-dimethyl-4-oxo-1,3,5-triazinan-1-yl)methyl)carbamat (1.04 g, 2.8 mmol, 1.0 equiv.), tetrabutylammonium iodide (0.11 g, 0.3 mmol, 0.10 equiv.), and KOH (85%, 0.37 g, 5.6 mmol, 2.0 equiv.) in a 1.4/1.0 mixture of CH$_2$Cl$_2$/H$_2$O (24.0 mL) was added dropwise with 3-iodobenzyl bromide (102 mg, 71 ul, 0.60 mmol, 1.2 equiv.) in THF (4.0 mL) over 1.5 h. The reaction was stirred at room temperature for 12 hours. At the completion of the reaction, the organic layer was separated and the aqueous layer was extracted with CH$_2$Cl$_2$ (20 mL×2). The combined organic extracts were washed with brine, dried over Na$_2$SO$_4$, filtered, and concentrated in vacuo. The residue was purified by flash chromatography (silica gel, EtOAc as eluent) to give the product (1.0 g, 61% yield) as a colorless solid. $^1$H NMR (400 MHz, CDCl$_3$) δ 7.71 (s, 1H), 7.66 (d, J=7.9 Hz, 1H), 7.30 (d, J=7.8 Hz, 1H), 7.07 (t, J=7.7 Hz, 1H), 4.46 (brs, 6H), 2.74 (brs, 6H), 1.53 (s, 9H), 1.47 (s, 9H); $^{13}$C NMR (100 MHz, CDCl$_3$) δ 158.7, 156.2, 151.9, 150.2, 135.8, 135.4, 134.3, 132.1, 128.1, 83.8, 81.7, 79.3, 60.8, 50.9, 32.1, 27.4, 24.3.

Example 14: Preparation of tert-butyl benzyl(((tert-butoxycarbonyl)imino)(3,5-dimethyl-4-oxo-1,3,5-triazinan-1-yl)methyl)carbamate

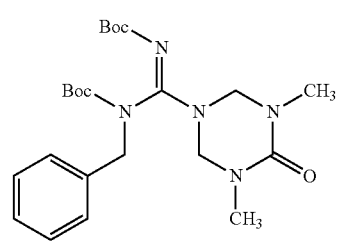 [SMILES: CN1CN(/C(=N/C(=O)OC(C)(C)C)N(Cc2ccccc2)C(=O)OC(C)(C)C)CN(C)C1=O]

This model compound was prepared from benzyl bromide using the procedure described in example 13. $^1$H NMR (300

MHz, CDCl₃) δ 7.40-7.27 (m, 5H), 4.43 (brs, 6H), 2.67 (brs, 6H), 1.53 (s, 9H), 1.46 (s, 9H); ¹³C NMR (75 MHz, CDCl₃) δ 158.6, 156.9, 152.1, 150.6, 136.2, 129.2, 128.9, 128.4, 82.7, 80.6, 77.4, 77.0, 76.6, 60.8, 51.2, 32.9, 28.2, 28.1; HRMS (ESI) Calcd for $C_{23}H_{35}N_5O_5$: 461.2638. Found: [M+Na]=484.2536.

Example 15: Preparation of tert-butyl (((tert-butoxycarbonyl)imino)(3,5-dimethyl-4-oxo-1,3,5-triazinan-1-yl)methyl)(3-flurobenzyl)carbamate

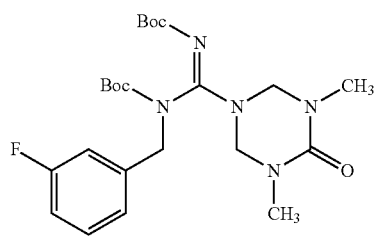 [SMILES: CN1CN(/C(=N/C(=O)OC(C)(C)C)N(Cc2cccc(F)c2)C(=O)OC(C)(C)C)CN(C)C1=O]

This compound was prepared from 3-fluorobenzyl bromide using the procedure described in example 13. (90%). ¹H NMR (400 MHz, CD₃CN) δ 7.40-7.32 (m, 1H), 7.19-7.03 (m, 3H), 4.45 (brs, 6H), 2.66 (brs, 6H), 1.48 (s, 9H), 1.43 (s, 9H); ¹³C NMR (100 MHz, CDCl₃) δ 163.8, 161.4, 158.8, 156.8, 152.0, 150.6, 138.9, 138.8, 130.6, 130.5, 125.3, 125.3, 116.1, 115.9, 115.0, 114.8, 82.2, 79.9, 60.7, 50.4, 32.1, 27.3, 27.3.

Example 16: Preparation of potassium tert-butyl (((tert-butoxycarbonyl)imino)(3,5-dimethyl-4-oxo-1,3,5-triazinan-1-yl)methyl)(3-(trifluoroboryl)benzyl) carbamate

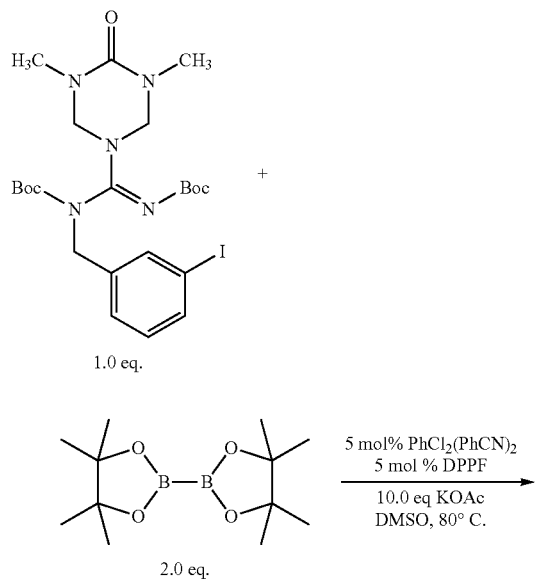

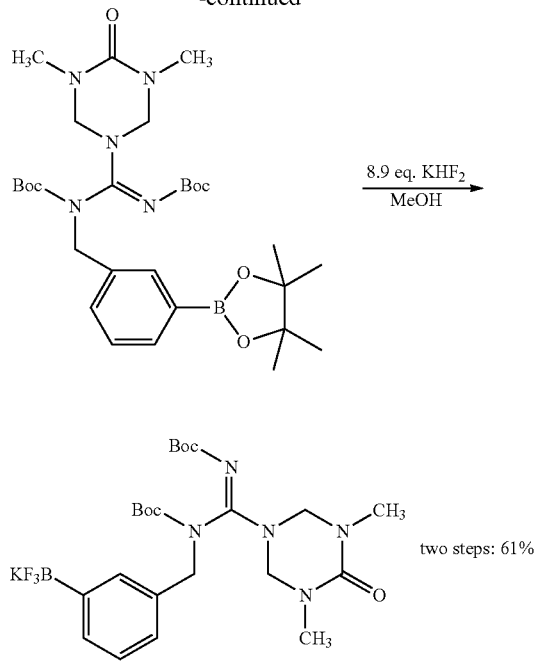

A flask charged with the iodoarene prepared in example 13 (1.20 g, 2.0 mmol, 1.0 equiv.), PdCl₂(PhCN)₂ (39 mg, 0.10 mmol, 0.05 equiv.), bis(diphenylphosphino)ferrocene (55 mg, 0.10 mmol, 0.05 equiv.), bispinacolatodiboron (1.02 g, 4.0 mmol, 2.0 equiv.) and KOAc 1.96 g, 20.0 mmol, 10.0 equiv.), was flushed with nitrogen and degassed DMSO (20 mL) was added. The mixture was heated at 80° C. and stirred for 12 hours, before the mixture was allowed to cool to room temperature. The mixture was extracted with ethyl acetate, washed with water, dried over anhydrous sodium sulfate, and concentrated. The crude tert-butyl (((tert-butoxycarbonyl)imino)(3,5-dimethyl-4-oxo-1,3,5-triazinan-1-yl)methyl) (3-(4,4,5,5-tetramethyl-1,3,2-dioxaborolan-2-yl)benzyl)carbamate was obtained as colorless solid (1.05 g) after flash column chromatography (silica gel, EtOAc as eluent to minimize the time of exposure to silica). ¹H NMR (400 MHz, acetone-d₆) δ 7.76 (s, 1H), 7.70 (d, J=7.4 Hz, 1H), 7.51 (d, J=7.5 Hz, 1H), 7.38 (t, J=7.5 Hz, 1H), 4.50 (brs, 6H), 2.66 (brs, 6H), 1.52 (s, 9H), 1.47 (s, 9H), 1.33 (s, 12H); ¹³C NMR (100 MHz, acetone-d₆) δ 158.6, 157.0, 152.1, 150.6, 138.5, 138.1, 137.4, 130.6, 128.4, 94.5, 83.1, 80.7, 61.0, 50.6, 33.0, 28.2, 28.1.

The above pinacol ester (1.05 g) was dissolved in MeOH (20 mL) to which a solution of KHF₂(aq) (1.24 g, 15.9 mmol, 4.5 M solution) was added over the course of 1.0 h. This mixture was stirred for an additional hour before dichloromethane was added to generate a white precipitate. The precipitate was removed by filtration and washed with DCM. The mother liquor was concentrated to yield 1.22 g of crude product as white solid. This white solid was washed with hexane to obtain the pure trifluoroborate salt (0.69 g, two steps 61%). ¹H NMR (500 MHz, CD₃CN) δ 7.38 (d, J=7.1 Hz, 1H), 7.35 (s, 1H), 7.14 (t, J=7.5 Hz, 1H), 7.07 (d, J=7.4 Hz, 1H), 4.91 (brs, 1H), 4.46 (brs, 3H), 4.01 (brs, 2H), 2.60 (brs, 6H), 1.94 (s, 9H), 1.44 (s, 9H); ¹³C NMR (100

MHz, CDCl$_3$) δ 158.9, 156.6, 152.0, 151.1, 133.9, 132.3, 131.3, 126.9, 126.2, 81.7, 79.7, 60.6, 51.6, 32.1, 27.4, 24.3.

Example 17: Preparation of 1-(Diacetoxyiodo)-4-methoxybenzene

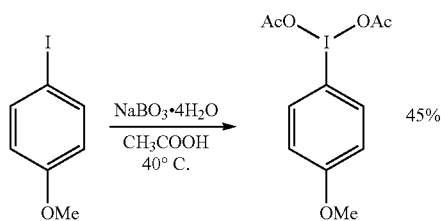 [SMILES: COc1ccc(I)cc1 ; COc1ccc(I(OC(C)=O)OC(C)=O)cc1]

4-Iodoanisole (2.34 g, 10 mmol) was dissolved in 90 mL of glacial acetic acid and the stirred solution was warmed to 40-45° C. Sodium perborate tetrahydrate (15.4 g, 110 mmol) was added in portions over the course of 3 h. After the addition was complete, the temperature of the reaction mixture was maintained at 40° C. overnight before it was allowed to cool to room temperature. The acetic acid (~30 mL) was removed by distillation at reduced pressure. The remaining solution was treated with 100 mL of deionized water and the aqueous layer was extracted (40 mL×3) with dichloromethane. The combined organic fractions were dried over sodium sulfate, and concentrated. The white solid was washed with hexane, then added 2 drops of glacial acetic acid and dried overnight in vacuo at 40° C. to give 1.60 g (45%) of 1-(diacetoxyiodo)-4-methoxybenzene. $^1$H NMR (400 MHz, CD$_3$CN): δ 8.06 (d, J=9.2 Hz, 2H), 7.05 (d, J=9.2 Hz, 2H), 3.86 (s, 3H), 1.91 (s, 6H).

Example 18: Preparation of (3-((N,N'-bis(tert-butoxycarbonyl)-3,5-dimethyl-4-oxo-1,3,5-triazinane-1-carboximidamido)methyl)phenyl)(4-methoxyphenyl)iodonium triflate

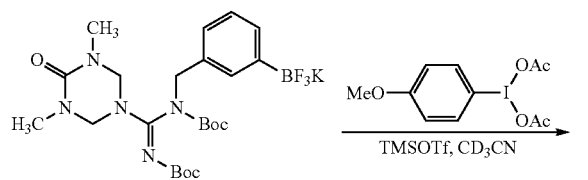

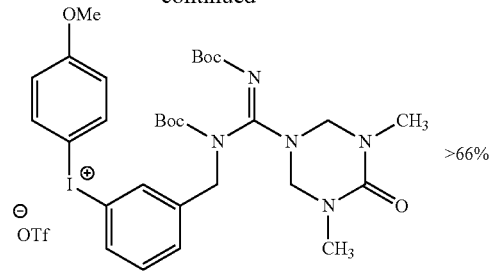

In a N$_2$ charged glove box, 1-(diacetoxyiodo)-4-methoxybenzene (224 mg, 0.64 mmol, 1.0 equiv.) was dissolved in 7.0 mL of dry CH$_3$CN. The solution was combined with a solution of the trifluoroborate salt (397 mg, 0.70 mmol, 1.1 equiv.) in 7.0 mL of dry CH$_3$CN. Trimethylsilyl triflate (155 mg, 0.70 mmol, 1.1 mmol) was added dropwise and the mixture was allowed to stand at room temperature for 30 min. Saturated aqueous sodium acetate (20 mL) was added and the mixture was extracted (3×20 mL) with CH$_2$Cl$_2$. The combined organic extracts were dried over sodium sulfate and concentrated. This compound was dissolved in 1 mL acetonitrile/water (9:1 by volume) solution and slowly passed down an Amberlite IRA-400 ion exchange column (triflate counterion). After removal of the solvents under reduced pressure, the purified iodonium triflate product was obtained by washing the colorless residue with pentane to remove any organic impurities The residue was recrystallized from dichloromethane to give 350 mg (66%) of the title iodonium triflate. $^1$H NMR (500 MHz, CD$_3$CN) δ 8.05 (d, J=8.0 Hz, 1H), 8.04 (d, J=9.2 Hz, 2H), 8.01-7.99 (m, 1H), 7.69 (d, J=7.8 Hz, 1H), 7.50 (t, J=8.0 Hz, 1H), 7.04 (d, J=9.2 Hz, 2H), 4.40 (brs, 6H), 3.83 (s, 3H), 2.60 (brs, 6H), 1.48 (s, 9H), 1.43 (s, 9H); $^{19}$F NMR (CD$_3$CN, 376 MHz): δ −79.3 (s, 3F).

Example 19: Iodination of (3-((N,N'-bis(tert-butoxycarbonyl)-3,5-dimethyl-4-oxo-1,3,5-triazinane-1-carboximidamido)methyl)phenyl)(4-methoxyphenyl)iodonium triflate in benzene

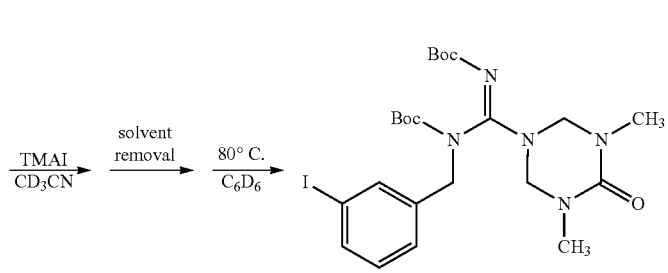

In a nitrogen atmosphere glove box, 0.020 mmol (17 mg) of iodonium triflate was dissolved in 0.5 mL of dry acetonitrile-$d_3$. A solution of 0.020 mmol (2 mg) of TMAI in 0.2 mL of dry acetonitrile-$d_3$ was added slowly. The mixture was transferred into a J-Young NMR tube, sealed, and taken out of the glove box. The solvent was evaporated and the tube was taken back into the glove box. Dry benzene-$d_6$ (0.6 mL) was added and transferred into a J-Young NMR tube, sealed, and taken out of the glove box. The tube was wrapped in aluminum foil and placed in an 80° C. oil bath. After 1 hour, no remaining starting material was observable by $^1$H NMR spectroscopy, and the characteristic signals of tert-butyl (((tert-butoxycarbonyl)imino)(3,5-dimethyl-4-oxo-1,3,5-triazinan-1-yl)methyl)(3-iodobenzyl)carbamates were visible.

Example 20: Iodination of (3-((N,N'-bis(tert-butoxycarbonyl)-3,5-dimethyl-4-oxo-1,3,5-triazinane-1-carboximidamido)methyl)phenyl)(4-methoxyphenyl)iodonium triflate in CD$_3$CN

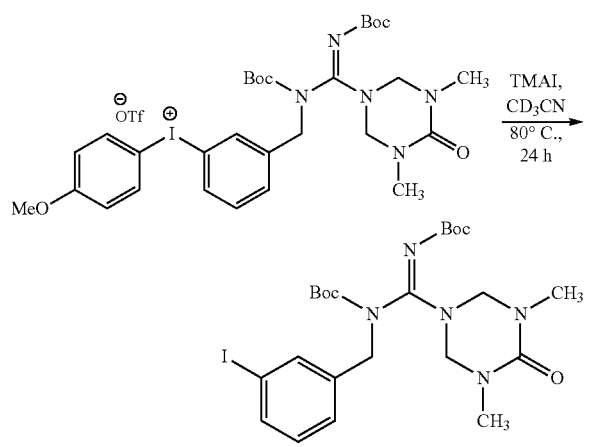

In a nitrogen atmosphere glove box, 0.020 mmol (17 mg) of iodonium triflate was dissolved in 0.5 mL of dry acetonitrile-$d_3$. A solution of 0.020 mmol (2 mg) of TMAI in 0.2 mL of dry acetonitrile-$d_3$ was added slowly. The mixture was transferred into a J-Young NMR tube, sealed, and taken out of the glove box, and the tube was wrapped in aluminum foil and placed in an 80° C. oil bath. The progress of the reaction was monitored by $^1$H NMR spectroscopy. After 24 hours, no remaining starting material was observable by $^1$H NMR spectroscopy, and the characteristic signals of tert-butyl (((tert-butoxycarbonyl)imino)(3,5-dimethyl-4-oxo-1,3,5-triazinan-1-yl)methyl)(3-iodobenzyl)carbamate were visible. This experiment indicated that polar solvents reduce the rate of iodination significantly, even under stoichiometric conditions.

Example 21: Iodination of (3-((N,N'-bis(tert-butoxycarbonyl)-3,5-dimethyl-4-oxo-1,3,5-triazinane-1-carboximidamido)methyl)-2,6-difluorophenyl)(4-methoxyphenyl)iodonium triflate in CD$_3$CN

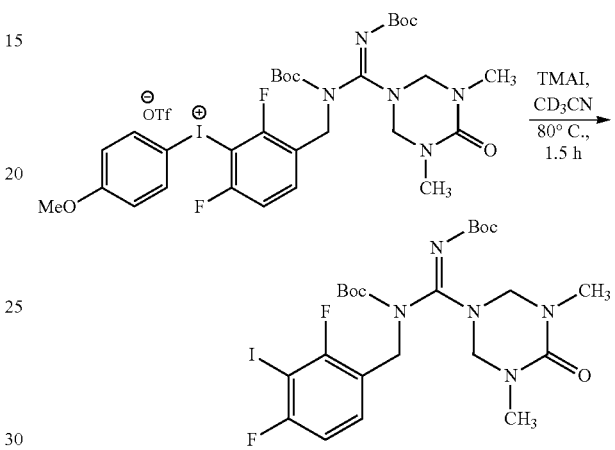

In a nitrogen atmosphere glove box, 0.020 mmol (17 mg) of iodonium triflate was dissolved in 0.5 mL of dry acetonitrile-$d_3$. A solution of 0.020 mmol (2 mg) of TMAI in 0.2 mL of dry acetonitrile-$d_3$ was added slowly. The mixture was transferred into a J-Young NMR tube, sealed, and taken out of the glove box, and the tube was wrapped in aluminum foil and placed in an 80° C. oil bath. The progress of the reaction was monitored by $^1$H NMR spectroscopy. After 90 minutes, no remaining starting material was observable by $^1$H NMR spectroscopy, and the characteristic signals of (E)-tert-butyl (((tert-butoxycarbonyl)imino)(3,5-dimethyl-4-oxo-1,3,5-triazinan-1-yl)methyl)(2,4-difluoro-3-iodobenzyl)carbamate were visible. This experiment indicated that the difluoro substitution pattern significantly enhances the rate of iodination significantly, even in polar solvents.

Example 22: $^{125}$I-Radioiodination of (3-((N,N'-bis(tert-butoxycarbonyl)-3,5-dimethyl-4-oxo-1,3,5-triazinane-1-carboximidamido)methyl)phenyl)(4-methoxyphenyl)iodonium triflate in toluene

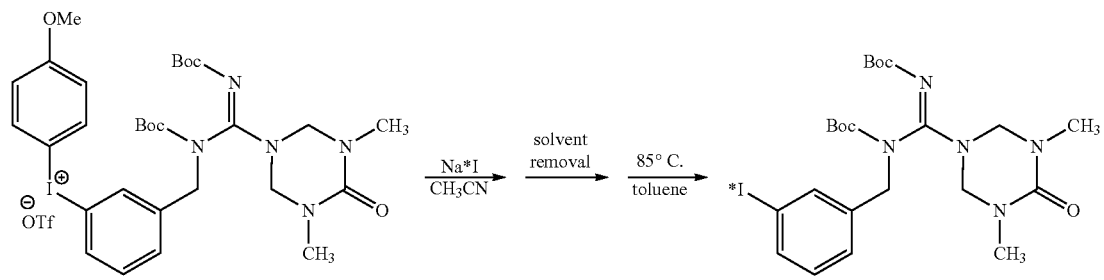

In a borosilicate vial, (3-((N,N'-bis(tert-butoxycarbonyl)-3,5-dimethyl-4-oxo-1,3,5-triazinane-1-carboximidamido)methyl)phenyl)(4-methoxyphenyl)iodonium triflate (15 mg) in 200 uL of acetonitrile was treated with aqueous Na$^{125}$I (1 uL sodium iodide solution, specific activity: ~17 Ci (629 GBq)/mg, 10$^{-5}$M NaOH (pH 8-11), 300 uCi total activity) dissolved in 200 uL of acetonitrile. The solvent was removed under reduced pressure. Toluene (250 uL) was added and the mixture was heated at 85° C. for 30 minutes. The solution was removed from the vial and spotted on a silica gel TLC plate, along with authentic standard (prepared in example 13). Elution of the product in 100% ethyl acetate showed the fully 94% of the activity was in the product, with 6% still present on the plate as Na$^{125}$I. However, an inventory of the activity showed that 90% of the initial activity (270 uCi) remained in vial and was not incorporated into the product. The total radiochemical yield of the product was 9.4%. This example indicates that nonpolar solvents lead to relatively poor incorporation of radioiodide if conventional, commercially available sodium salts are used.

Example 23: $^{125}$I-Radioiodination of (3-((N,N'-bis(tert-butoxycarbonyl)-3,5-dimethyl-4-oxo-1,3,5-triazinane-1-carboximidamido)methyl)phenyl)(4-methoxyphenyl)iodonium triflate in 10% acetonitrile/toluene

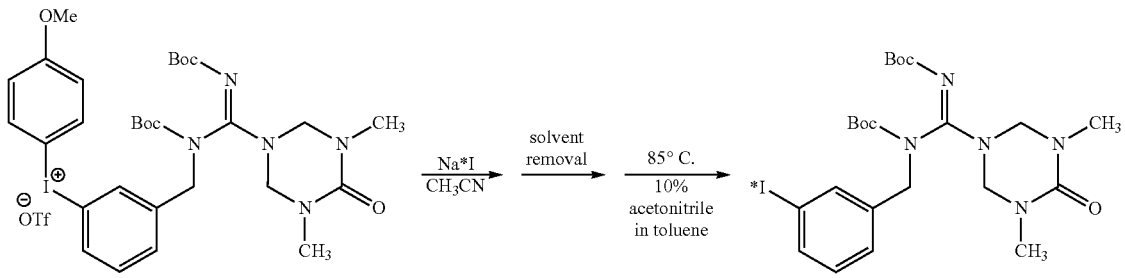

In a borosilicate vial, (3-((N,N'-bis(tert-butoxycarbonyl)-3,5-dimethyl-4-oxo-1,3,5-triazinane-1-carboximidamido)methyl)phenyl)(4-methoxyphenyl)iodonium triflate (15 mg) in 200 uL of acetonitrile was treated with aqueous Na$^{125}$I (1 uL sodium iodide solution, specific activity: ~17 Ci (629 GBq)/mg, 10$^{-5}$M NaOH (pH 8-11), 300 uCi total activity) dissolved in 200 uL of acetonitrile. The solvent was removed under reduced pressure. A solution of acetonitrile (25 uL) in toluene (225 uL) was added and the mixture was heated at 85° C. for 30 minutes. The solution was removed from the vial and spotted on a silica gel TLC plate, along with authentic standard (prepared in example 13). Elution of the product in 100% ethyl acetate showed almost quantitative incorporation of the activity into the product with no residual Na$^{125}$I. An inventory of the activity showed almost no residual activity in the vial, and 291 uCi in the product solution. The total radiochemical yield of the product was 97%. This example indicates that a mixture incorporating a small amount of polar solvent in the nonpolar solvent leads to excellent incorporation of radioiodide with conventional, commercially available sodium salts. Moreover, the rate of reaction does not suffer significantly if a small amount of polar solvent is added.

Example 24: $^{125}$I-Radioiodination of (3-((N,N'-bis(tert-butoxycarbonyl)-3,5-dimethyl-4-oxo-1,3,5-triazinane-1-carboximidamido)methyl)phenyl)(4-methoxyphenyl)iodonium triflate in 10% acetonitrile/toluene Using a Small Amount of Precursor

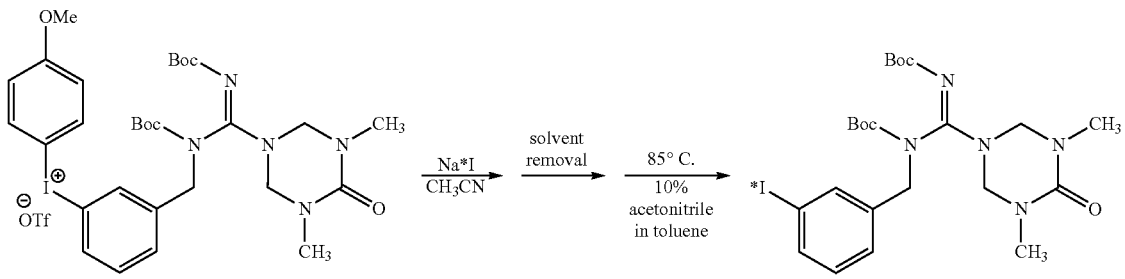

In a borosilicate vial, (3-((N,N'-bis(tert-butoxycarbonyl)-3,5-dimethyl-4-oxo-1,3,5-triazinane-1-carboximidamido)methyl)phenyl)(4-methoxyphenyl)iodonium triflate (1 mg) in 200 uL of acetonitrile was treated with aqueous $Na^{125}I$ (1 uL sodium iodide solution, specific activity: ~17 Ci (629 GBq)/mg, $10^{-5}$M NaOH (pH 8-11), 300 uCi total activity) dissolved in 200 uL of acetonitrile. The solvent was removed under reduced pressure. A solution of acetonitrile (25 uL) in toluene (225 uL) was added and the mixture was heated at 85° C. for 30 minutes. The solution was removed from the vial and spotted on a silica gel TLC plate, along with authentic standard (prepared in example 13). Elution of the product in 100% ethyl acetate showed 90% incorporation of the activity into the product, 5% residual $Na^{125}I$, and 5% $^{125}I$-4-iodoanisole. An inventory of the activity showed almost no residual activity in the vial, and ~290 uCi in the product solution. The total radiochemical yield of the product was 87%. This example indicates that a reduced amount of substrate still provided good incorporation of the label, but that selectivity and yield are lower under these conditions.

Example 25: Comparison of Iodination of Diaryliodonium Salts with Fluorination, Chlorination, and Bromination Each of the four bis(4-methoxyphenyl)iodonium halides (fluoride, chloride, bromide, iodide) (10 mg) was suspended in $C_6D_6$, sealed in a J. Young NMR tube, and heated at 120° C. for the times indicated: (fluoride, 2.5 hours; chloride, 5 days; bromide, 5 hours, iodide, 2.5 hours). The reactions were followed by $^1H$ NMR spectroscopy and were deemed completed when a homogeneous solution containing no trace of the diaryliodonium salt starting material was obtained. Representative $^1H$ NMR spectra obtained at the completion of reactions are show in FIG. 1.

Different reactivity modes are observed across the series of halides. Thermal decomposition of the diaryliodonium fluoride in $d_6$-benzene gave mostly 4-fluoroanisole and a small amount of 3-fluoroanisole. This side product probably arises from a competing mechanism that involves a benzyne intermediate formed by ortho-proton extraction by the hard base fluoride under these conditions. In contrast, chloride and bromide reacted to provide the corresponding 4-haloanisole in quantitative yield; no 3-halo regioisomers were produced. This can be explained easily; the basicity of chloride and bromide are not high enough to promote benzyne formation by proton abstraction. In contrast to these three reactions, which appear to proceed through two-electron intermediates, the thermal decomposition of bis(4-methoxyphenyl)iodonium iodide produces 4,4'-dimethoxybiphenyl, $I_2$, and an unidentified arene product in addition to the 4-iodoanisole. The biphenyl and $I_2$ probably result from the formation of free radical intermediates.

Example 26: $^{124}I$-Radioiodination—General Procedure for the Preparation of $^{124}I$-Labeled Benzylguanidine Derivatives

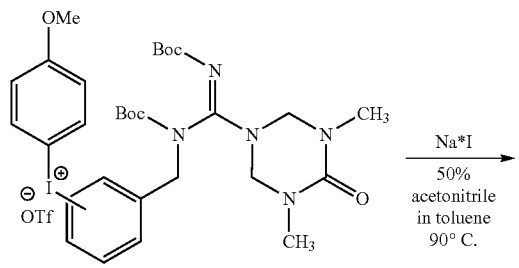

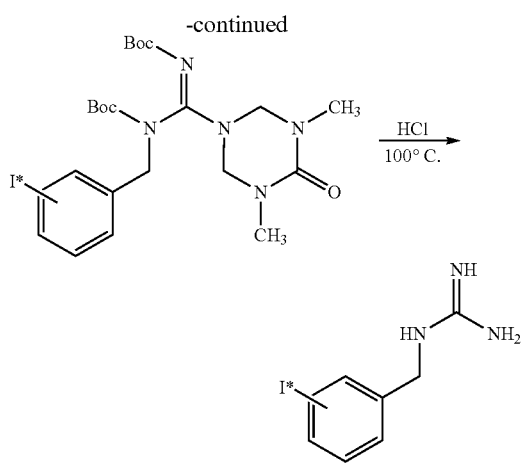

Preparation of Iodide Solution:

Aqueous $Na^{124}I$ was dissolved in 0.1M NaOH. 1 μl of $Na^{124}I$ (Na*I; approximately 1 mCi) was added to a reaction vial along with 1 μl of 1.0 M AcOH to prepare an acidic, slightly buffered solution. Because the volume of water was so small, initial drying of the Na*I solution was not required. (For larger scale reactions that involve more water, an azeotropic drying procedure with 400 μl of $CH_3CN$ was performed before the labeling step.)

Labeling:

5 mg of the protected diaryliodonium precursor was dissolved in 400 μl of $CH_3CN$. The mixture was allowed to stand for 10 minutes to make certain all of the crystalline substrate had dissolved. The dissolved precursor was added to the reaction vial and the solution was evaporated with a stream of dry argon at 90° C. (approximately two minutes). After the solvent was removed completely, 125 μL of $CH_3CN$ was added (with shaking or stirring) to dissolve the salts. Toluene (125 μL) was added and the solution was heated at 90° C. for 30 minutes. Silica TLC (100% ethyl acetate) was performed to determine the labeling efficiency.

Intermediate Purification:

A silica gel sep-pak plus was treated with hexanes (2×2 mL) such that hexanes remained on the sep-pak. (The sep-pak was not blown dry). The reaction mixture was introduced to the sep-pak, followed by 3 mL of 1:1 toluene:acetonitrile. The eluent was collected and radioTLC analysis (Silica, 100% ethyl acetate) showed that almost all of the iodide salt was removed from the mixture. The solvents were evaporated (under vacuum with a stream of argon at 90° C.). Full evaporation of the solvent from the 4 mL reactor vial took approximately 30 minutes.

Deprotection:

The residue in the reactor vial was dissolved in 200 μl of 6M HCl, and heated at 100° C. for 10 minutes. The solution was allowed to cool for one minute and neutralized with 120 μl of 10M NaOH. A reverse phase (C18) sep pak was rinsed with ethanol (10 mL) and water (10 mL) and blown dry. The neutralized solution (pH-2) was passed through the sep pak and the sep pak was rinsed with 2 mL of water (to elute any remaining salts) and blown dry. Ethanol (0.8 mL) was passed through the sep pak to elute the radiolabeled benzylguanidine derivative. Ethanol was removed using a stream of nitrogen before the material was purified by HPLC.

Semipreparative HPLC of the Crude Reaction Mixture:

The analysis and final HPLC was performed using an Alltech Econosphere C18 chromatography column (250×4.6 mm) and the product was eluted with 50% acetonitrile/50% 20 mmol ammonium acetate at a flow rate of 1.5 mL per minute.

Post HPLC Isolation:

The collected fraction was diluted with 20 mL H$_2$O and the radiolabeled product was trapped on a second C18 sep pak. The cartridge was rinsed with distilled water, blown dry, and the product was eluted in 0.8 mL of ethanol.

Example 27: Preparation of $^{124}$I-MIBG

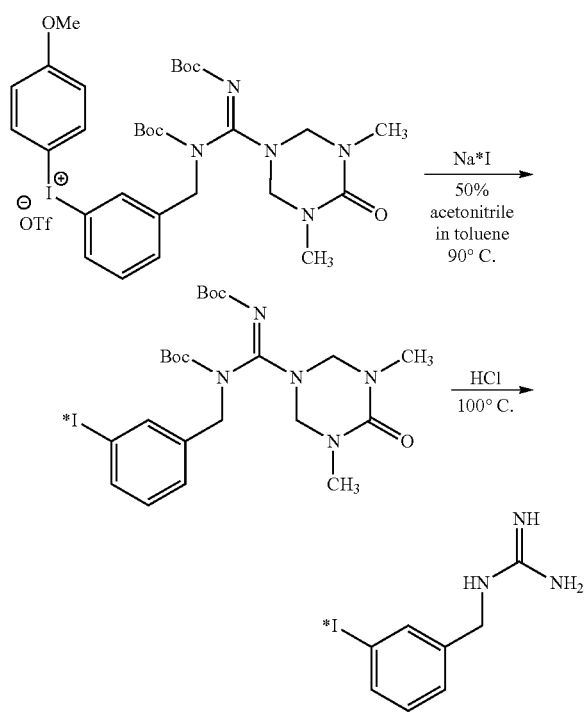

$^{124}$I-MIBG was prepared in 74±5% radiochemical yield (n=8) at the 1-2 mCi scale using the procedure outlined in Example 26. The retention time for the labeled final product semipreparative HPLC purification was 7.3 minutes. Following isolation, the product was >99% chemically and radiochemically pure, as assayed by HPLC.

Example 28: Preparation of $^{124}$I-2,4-difluoro-3-iodobenzylguanidine

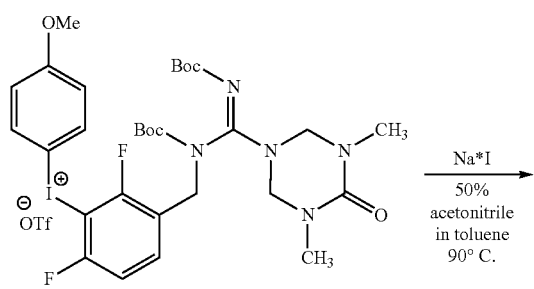

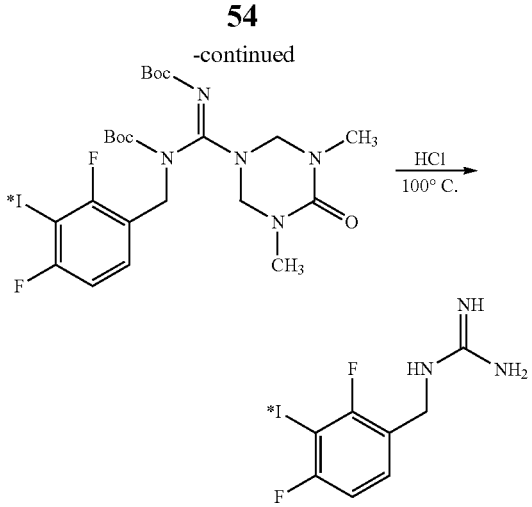

124I-2,4-difluoro-3-iodobenzylguanidine was prepared in 80±6% radiochemical yield (n=4) at the 1-2 mCi scale using the procedure outlined in Example 26. Following isolation, the product was >99% chemically and radiochemically pure, as assayed by HPLC. Compared to MIBG, the difluorinated compound showed greater thermal stability to iodine loss during the deprotection reaction, so the yields of final product obtained was significantly higher.

Example 29: Preparation of $^{124}$I-4-iodobenzylguanidine

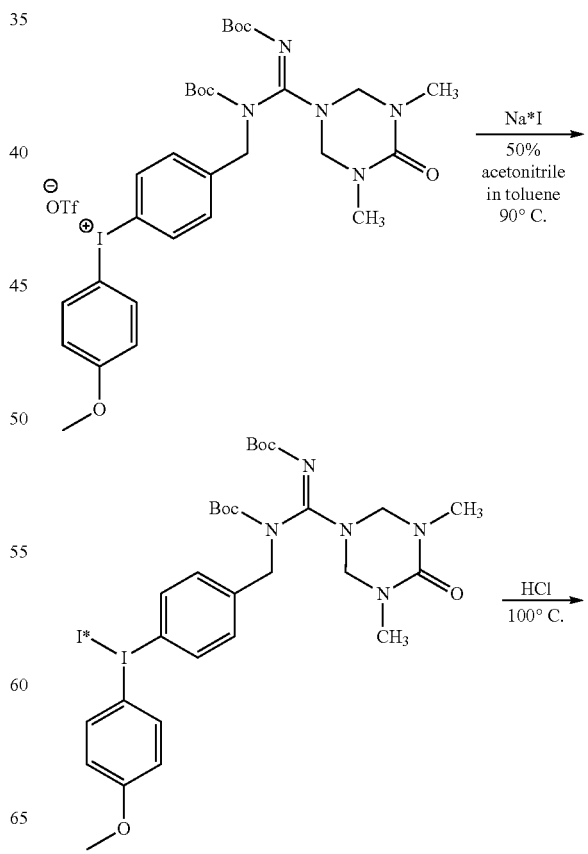

-continued

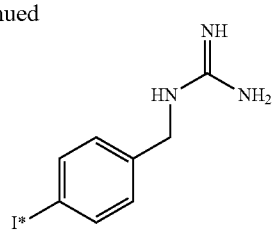

$^{124}$I-4-iodobenzylguanidineIBG was prepared in 62±6% radiochemical yield (n=4) at the 1-2 mCi scale using the procedure outlined in Example 26. Following isolation, the product was >99% chemically and radiochemically pure, as assayed by HPLC.

Example 30: Preparation of $^{124}$I-4-iodo-3,5-difluorobenzylguanidine

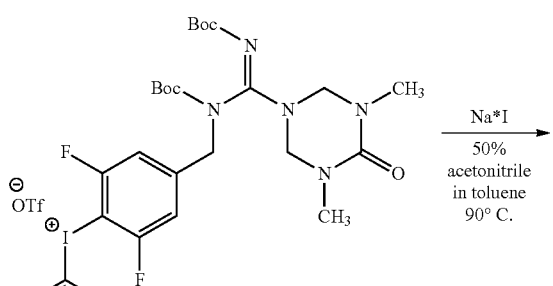

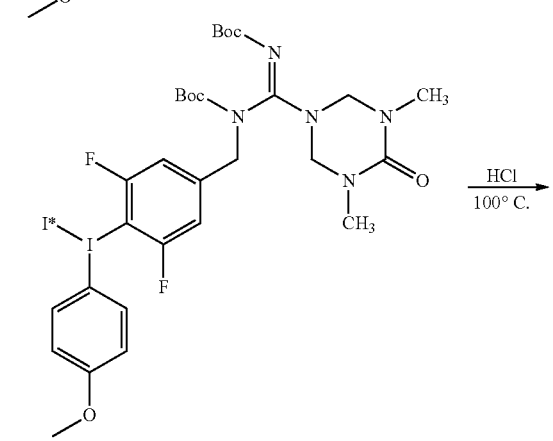

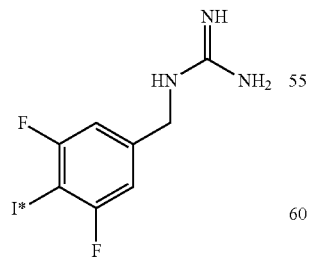

$^{124}$I-4-iodo-3,5-difluorobenzylguanidine was prepared in 70±7% radiochemical yield (n=4) at the 1-2 mCi scale using the procedure outlined in Example 26. Following isolation, the product was >99% chemically and radiochemically pure, as assayed by HPLC.

Example 31: Imaging and Biodistribution Study of 124-MIBG Prepared Using Two Methods To determine whether the method of preparation of MIBG affected the biodistribution of the compound, high specific activity $^{124}$I-MIBG was prepared using the diaryliodonium salt method (Example 27) and the conventional stannylated resin precursor; these compounds were imaged in rodent models.

Eight male Sprague-Dawley rats were used for the study. Upon arrival at the laboratory, each animal was inspected, uniquely identified with the animal number written on their tails, and weighed. The animals were judged to be in good health and were immediately placed in acclimation. Animals were between 6-14 weeks of age and weighed 440.5±36.4 g.

After a single intravenous dose of $^{124}$I-MIBG prepared by diaryliodonium salt precursor, or $^{124}$I-MIBG prepared with conventional method, Sprague-Dawley rats were given PET/CT scans at 1, 4, and 24 hours post injection of radiotracer. Biodistribution analysis was performed to quantify the amount of uptake in each animal's heart, liver, kidneys, thyroid, quadriceps muscle, and whole body as a function of time. Data is presented in units of µCi, µCi/mm3, % ID, and % ID/g. The radiochemical purity of all compounds as assessed by HPLC was >97% within an hour of administration. There was no noted qualitative or quantitative difference in the biodistribution of $^{124}$I-MIBG prepared by diaryliodonium salt precursor and $^{124}$I-MIBG prepared by a conventional method.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A method for making a compound of Formula (1):

$$Ar^2\text{—}*I \qquad 1$$

wherein:
Ar$^2$ is an aryl or heteroaryl ring system; and
I* is a radioactive isotope of iodine;
wherein the radioactive isotope of iodine has a specific activity of at least about 1 mCi/mg;
the method comprising:
(a) reacting a mixture comprising a compound M*I, wherein M is a counter cation, and compound of Formula (2):

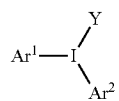

wherein:
Ar$^1$ is an aryl or heteroaryl ring system that is electron-rich as compared to Ar$^2$;
Y is a leaving group; and
Ar$^2$ is as defined above; and
(b) heating the reaction mixture from step (a).

2. The method of claim 1, wherein the reaction mixture in step (a) further comprises a solvent.

3. The method of claim 2, wherein the solvent is removed from the reaction mixture prior to step (b).

4. The method of claim 1, wherein the reaction mixture in step (b) further comprises a solvent.

5. The method of claim 1, wherein Ar$^1$—H is more easily oxidized than benzene.

6. The method of claim 1, wherein Ar$^1$ is substituted with at least one substituent having a Hammett $\sigma_p$ value of less than zero.

7. The method of claim 6, wherein the substituent is selected from the group consisting of: —(C$_1$-C$_{10}$)alkyl, —(C$_1$-C$_{10}$)haloalkyl, (C$_2$-C$_{10}$)alkenyl, (C$_2$-C$_{10}$)alkynyl, —O—(C$_1$-C$_{10}$)alkyl, —C(O)—O—(C$_1$-C$_{10}$)alkyl, aryl, and heteroaryl.

8. The method of claim 1, wherein the radioactive isotope of iodine is selected from the group consisting of: $^{123}$I, $^{124}$I, $^{125}$I, and $^{131}$I.

9. The method of claim 1, wherein Ar$^1$ is:

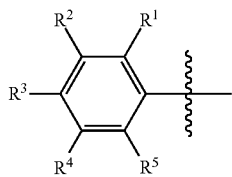

wherein:
R$^1$, R$^2$, R$^3$, R$^4$, and R$^5$ are independently selected from the group consisting of: H, —(C$_1$-C$_{10}$)alkyl, —(C$_1$-C$_{10}$)haloalkyl, ((C$_2$-C$_{10}$)alkenyl, (C$_2$-C$_{10}$)alkynyl, —O—(C$_1$-C$_{10}$)alkyl, —C(O)—O—(C$_1$-C$_{10}$)alkyl, aryl, and heteroaryl, or two or more of R$^1$, R$^2$, R$^3$, R$^4$, and R$^5$ come together to form a fused aryl or heteroaryl ring system.

10. The method claim 1, wherein AP is selected from the group consisting of: a phenylalanine derivative, tyrosine derivative, tryptophan derivative, histidine derivative, and an estradiol derivative.

11. The method of claim 1, wherein AP is selected from the group consisting of:

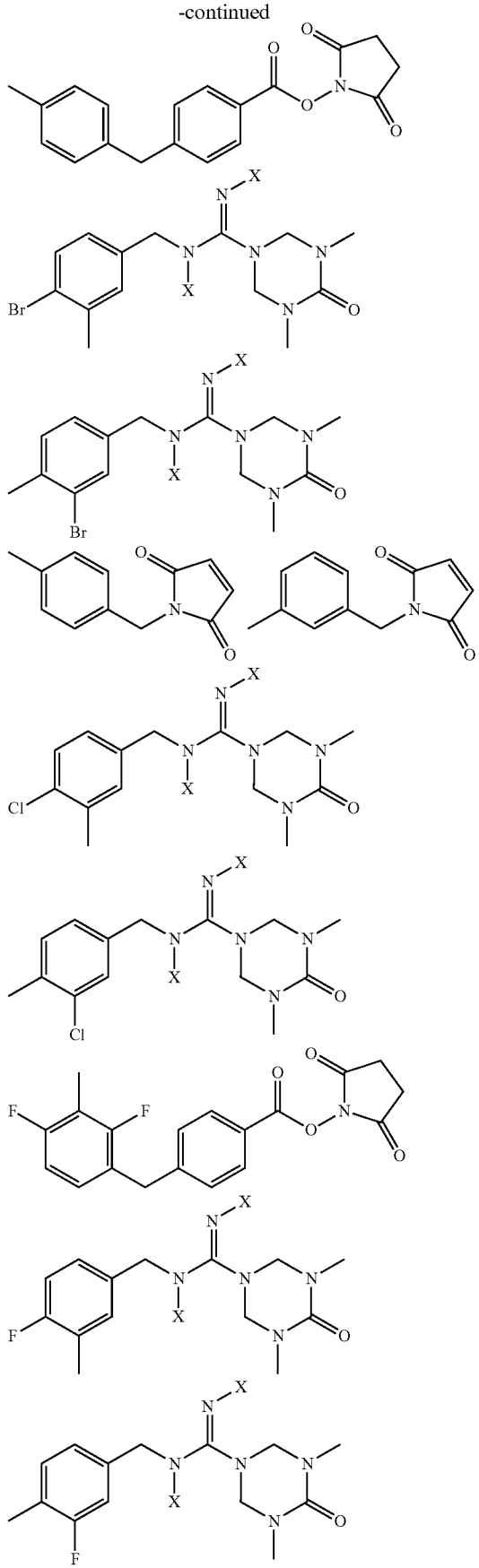

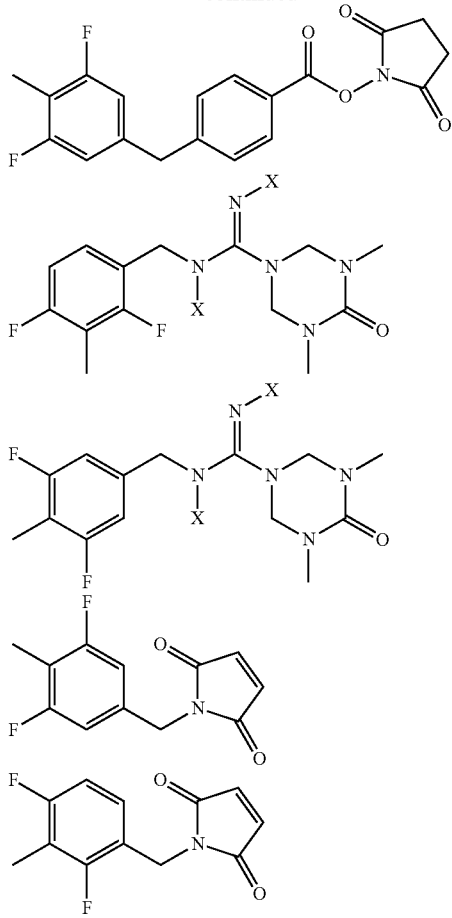

wherein each X is independently a protecting group.

12. The method of claim 11, wherein Ar² is selected from the group consisting of:

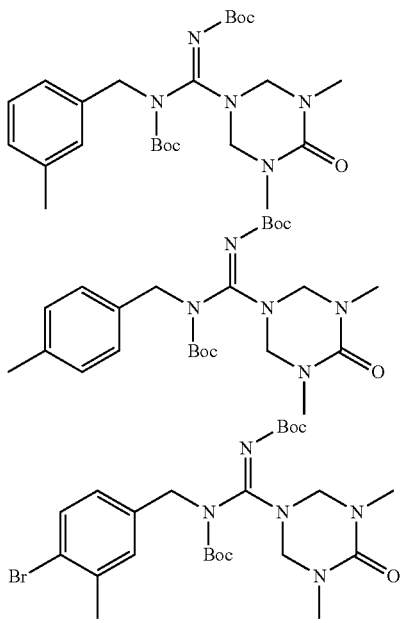

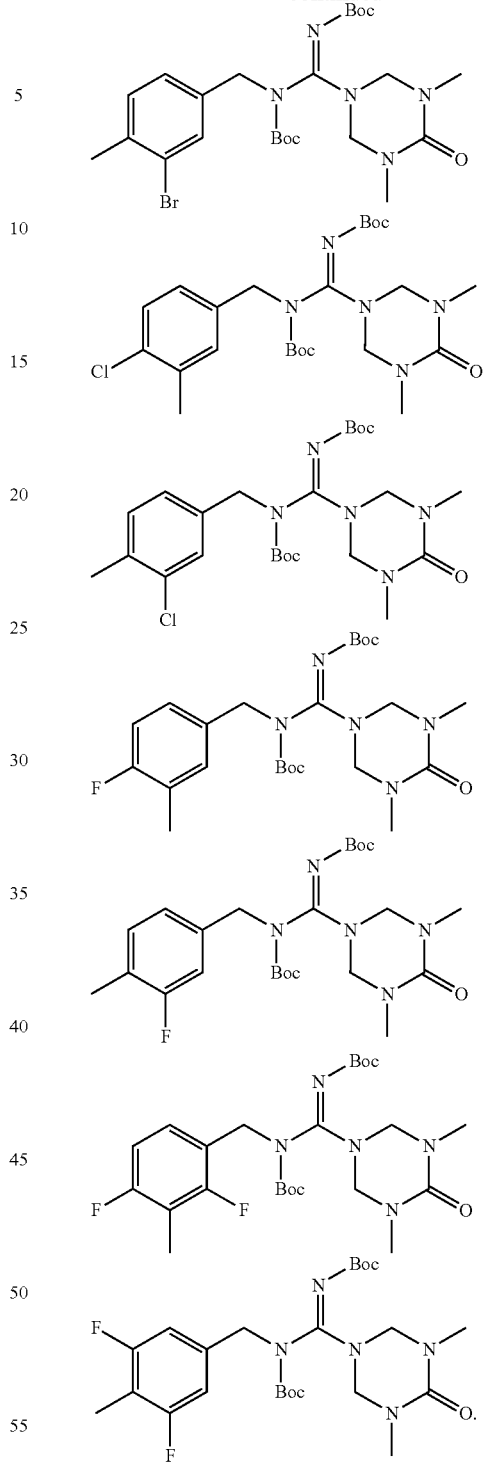

13. The method of claim 1, wherein Y is selected from the group consisting of: triflate, mesylate, nonaflate, hexaflate, tosylate, nosylate, brosylate, perfluoroalkyl sulfonate, tetraphenylborate, hexafluorophosphate, trifluoroacetate, tetrafluoroborate, perchlorate, perfluoroalkylcarboxylate, and chloride.

14. The method of claim 1, wherein M is selected from the group consisting of: lithium, potassium, sodium, cesium, complexes of lithium, sodium, potassium, or cesium with cryptands or crown ethers, tetrasubstituted ammonium cations, and phosphonium cations.
15. The method of claim 1, wherein the compound of Formula (2) is selected from the group consisting of:
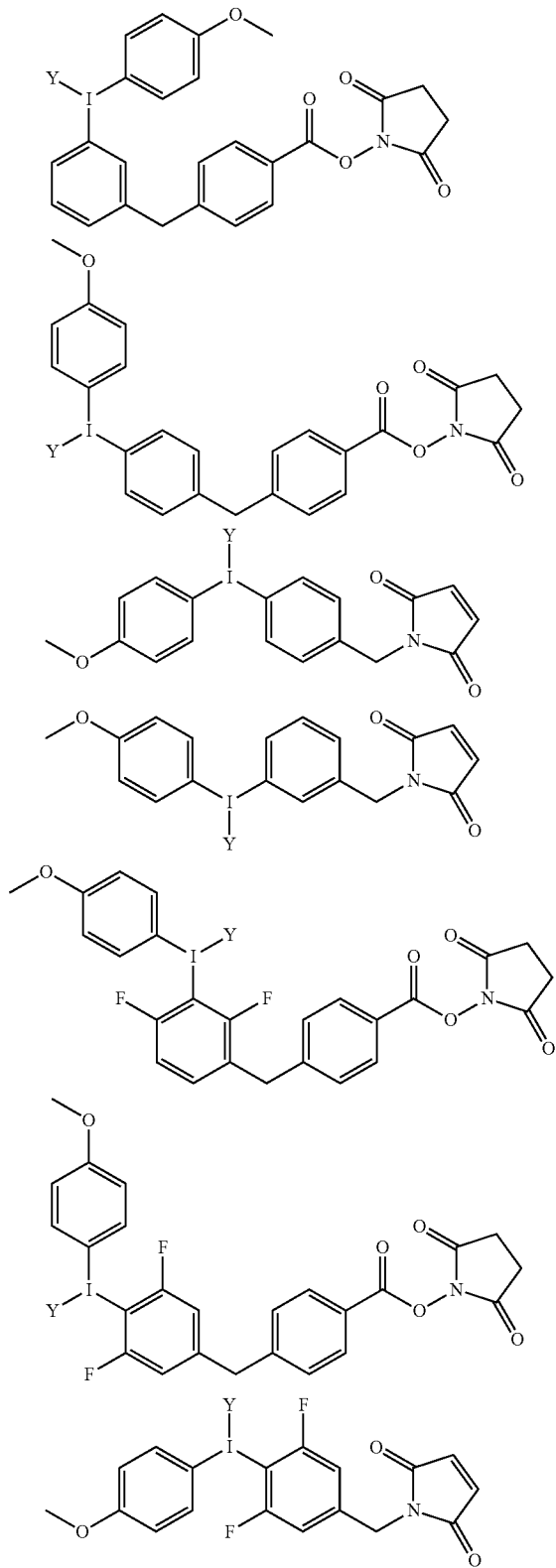
-continued
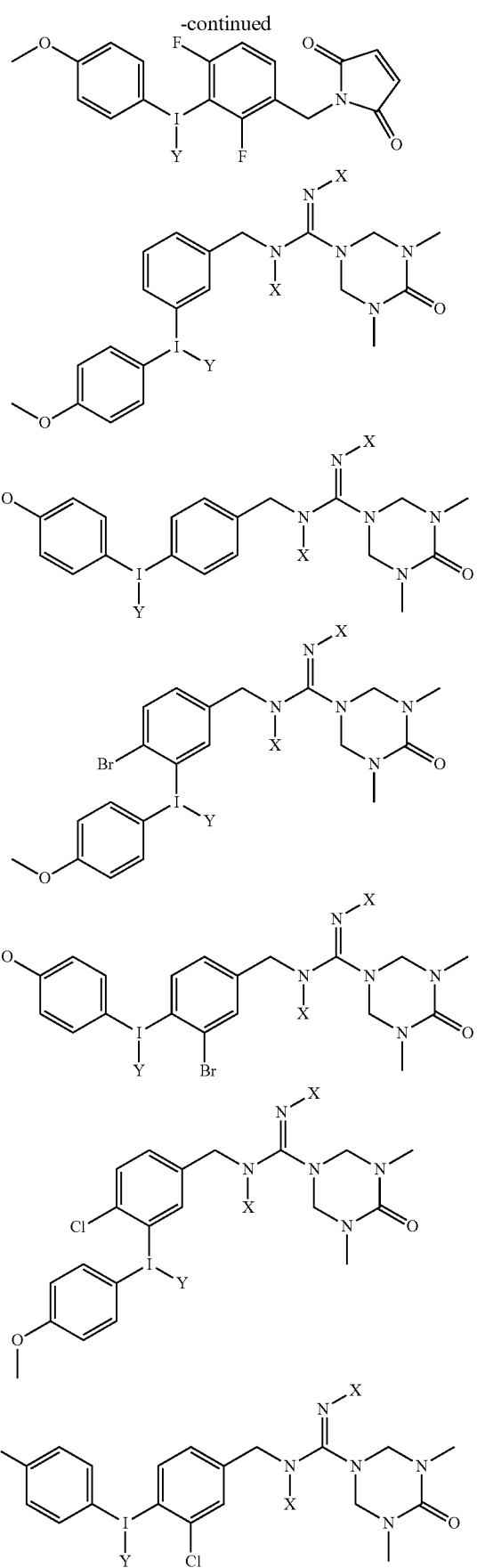

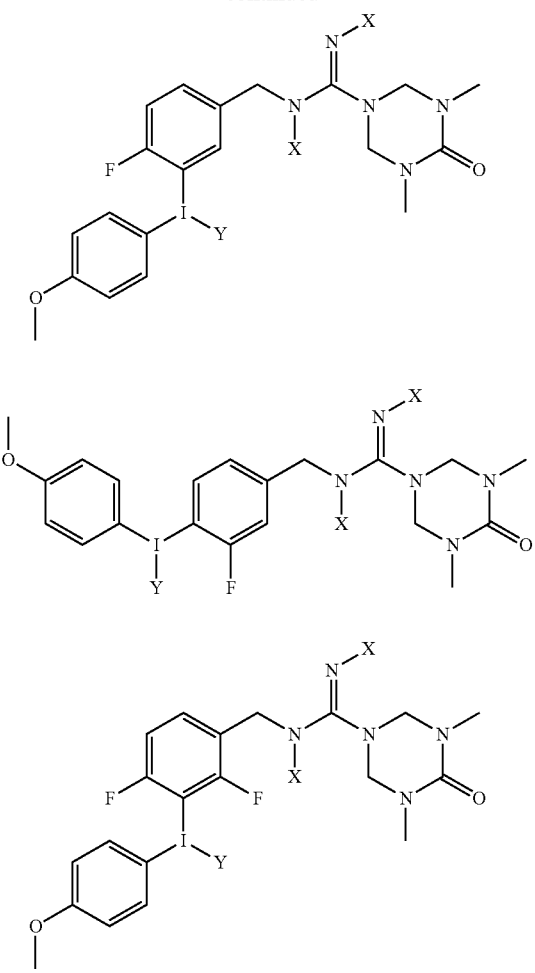
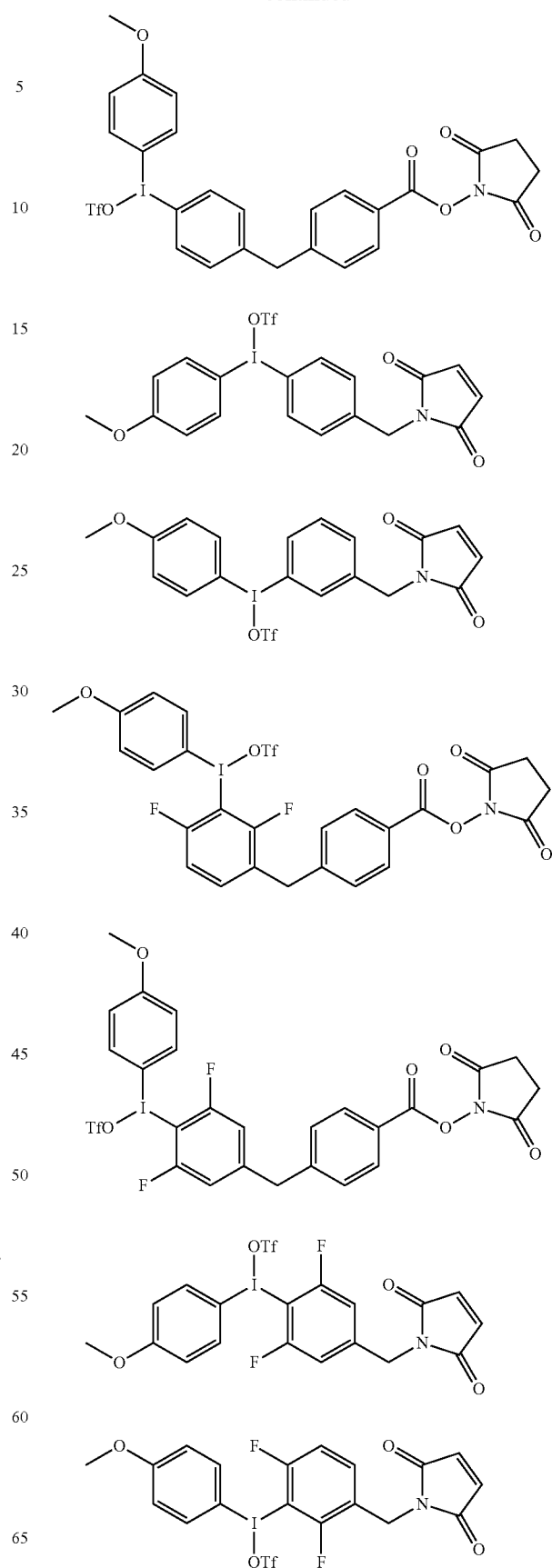
wherein each Y is independently a leaving group as defined above; and
each X is independently a protecting group.
16. The method of claim 15, wherein the compound of Formula (2) is selected from the group consisting of:
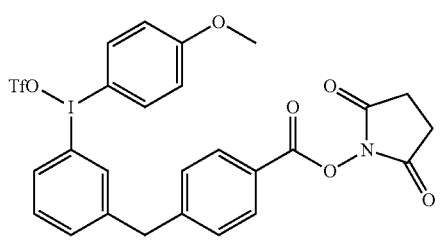

-continued
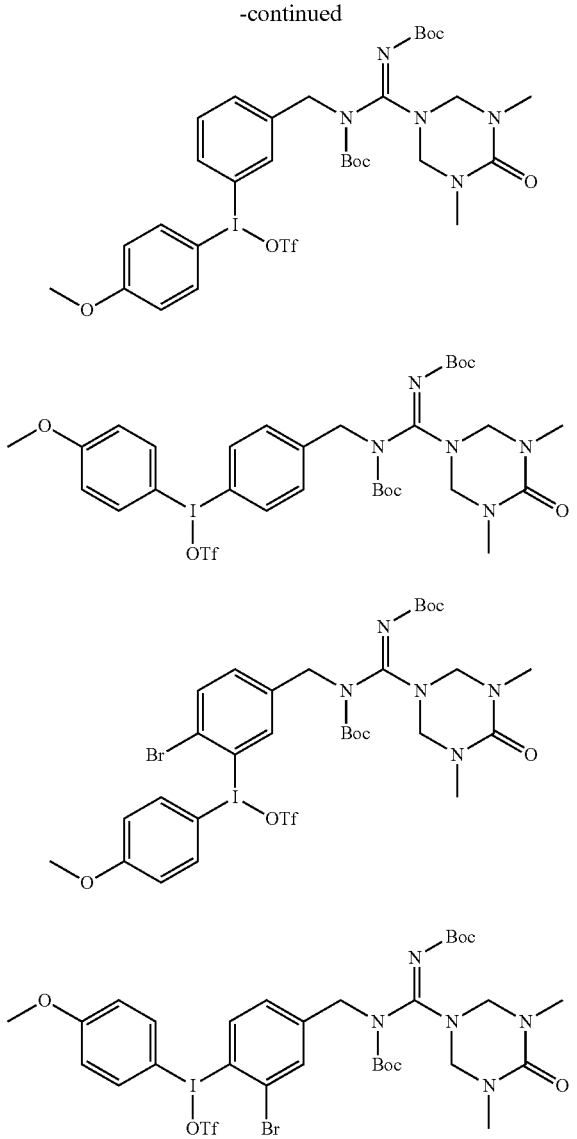
-continued
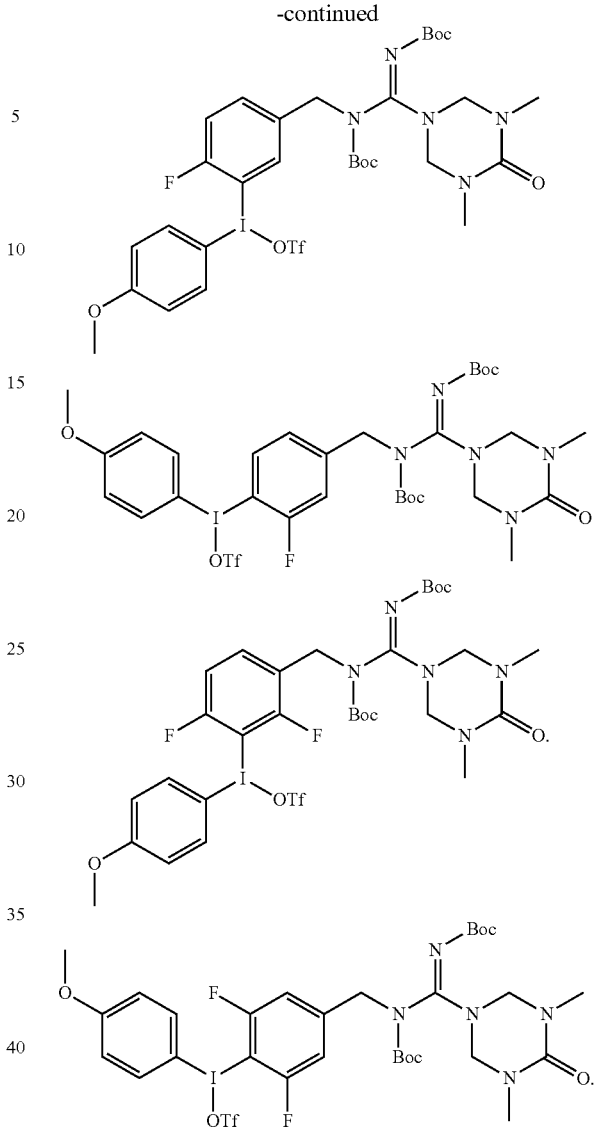
17. The method of claim 1, wherein the compound of Formula (1) is selected from the group consisting of:
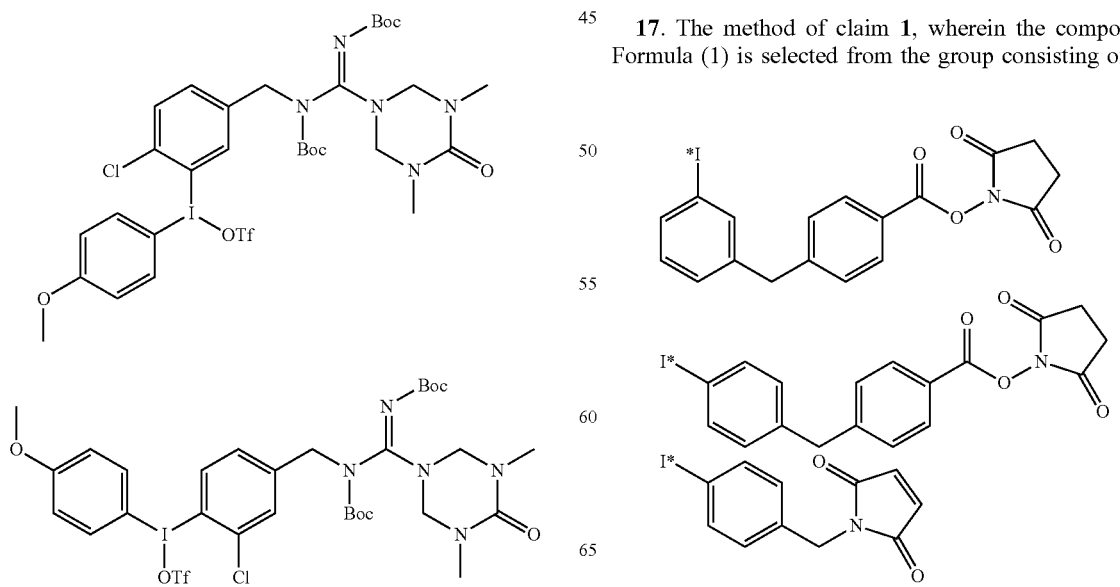

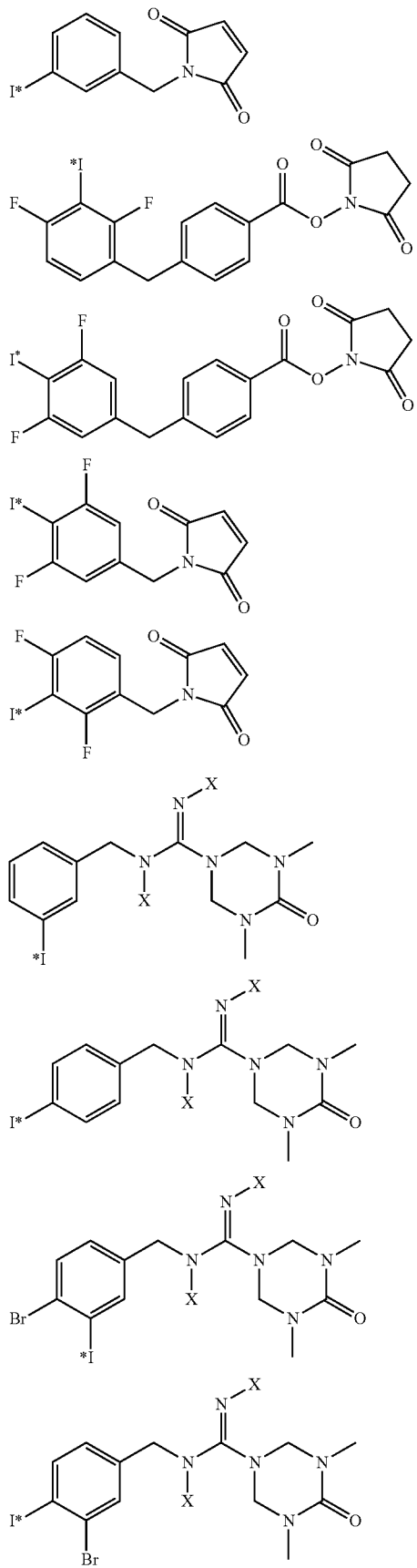
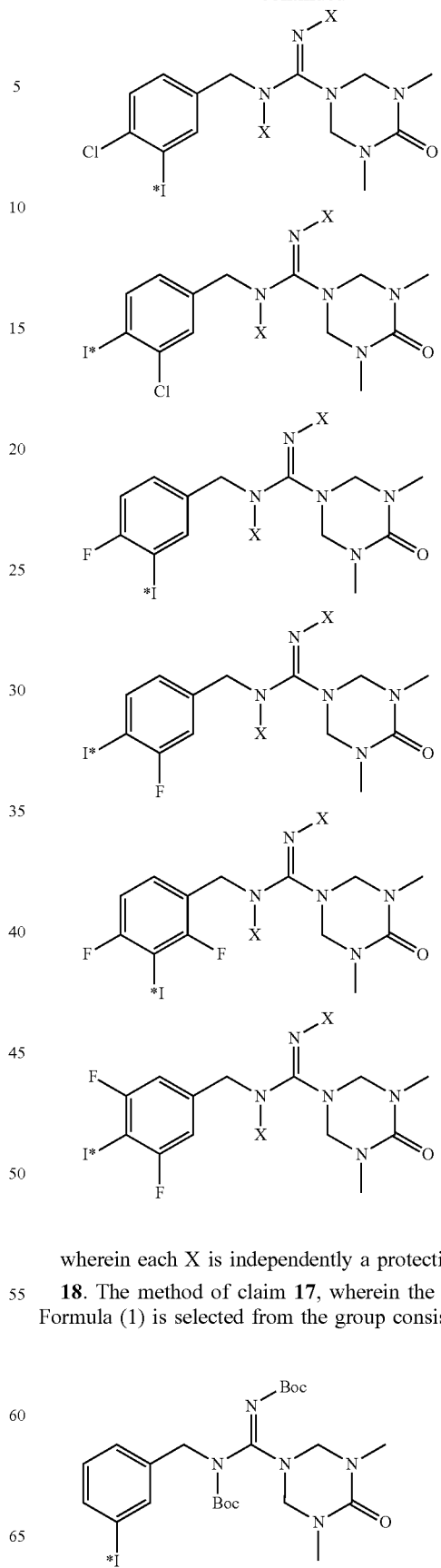
wherein each X is independently a protecting group.
18. The method of claim 17, wherein the compound of Formula (1) is selected from the group consisting of:

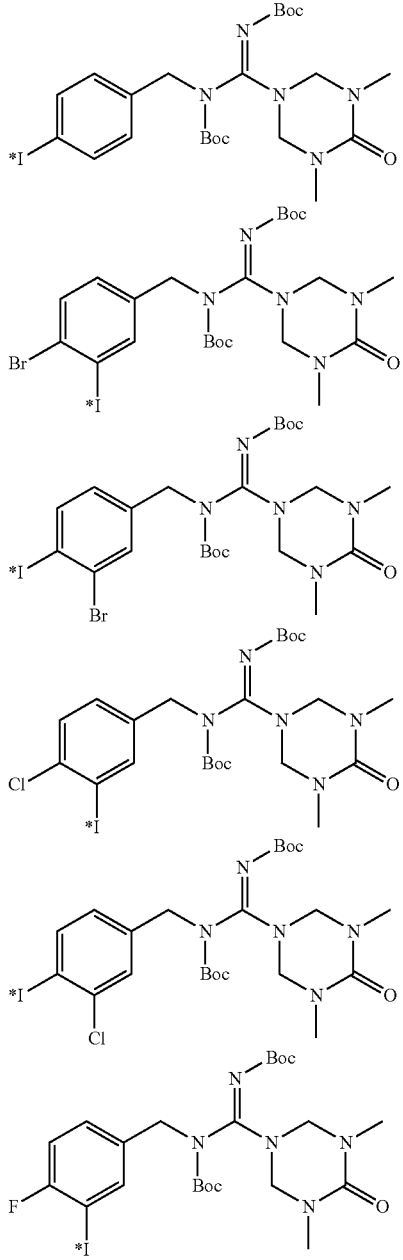

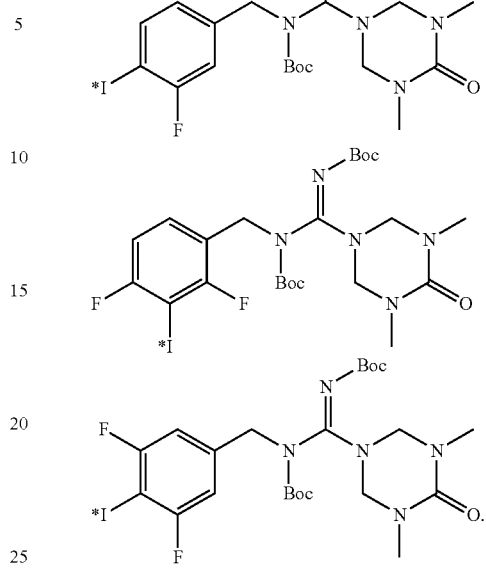

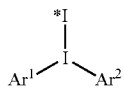

19. A method for making a compound of Formula (1)

$$Ar^2-*I \qquad (1)$$

wherein:
Ar² is an aryl or heteroaryl ring system; and
*I is a radioactive isotope of iodine;
  wherein the radioactive isotope of iodine has a specific activity of at least about 1 mCi/mg;
the method comprising heating a compound of Formula (3):

$$Ar^1 \overset{*I}{\underset{}{\diagup}} I \diagdown Ar^2 \qquad (3)$$

wherein:
Ar¹ is an aryl or heteroaryl ring system that is electron-rich as compared to Ar²; and
Ar² is as defined above.

* * * * *

UNITED STATES PATENT AND TRADEMARK OFFICE
CERTIFICATE OF CORRECTION

PATENT NO.         : 10,053,423 B2
APPLICATION NO.    : 15/109608
DATED              : August 21, 2018
INVENTOR(S)        : Stephen DiMagno et al.

Page 1 of 3

It is certified that error appears in the above-identified patent and that said Letters Patent is hereby corrected as shown below:

In Column 57 Line 33 (approx.) In Claim 9, delete "(($C_2$-$C_{10}$)alkenyl," and insert --($C_2$-$C_{10}$)alkenyl,--, therefor.

In Column 57 Line 38 (approx.) In Claim 10, after "method" insert --of--.

In Column 57 Line 38 (approx.) In Claim 10, delete "AP" and insert --$Ar^2$--, therefor.

In Column 57 Line 41 In Claim 11, delete "AP" and insert --$Ar^2$--, therefor.

In Column 57 Line 55-65 (approx.) In Claim 11, please delete

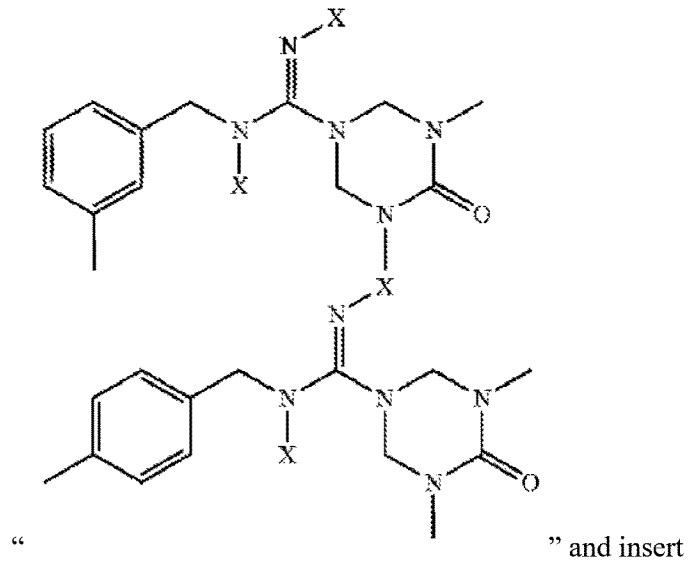

" " and insert

Signed and Sealed this
Tenth Day of December, 2019

Andrei Iancu
*Director of the United States Patent and Trademark Office*

CERTIFICATE OF CORRECTION (continued)
U.S. Pat. No. 10,053,423 B2

Page 2 of 3

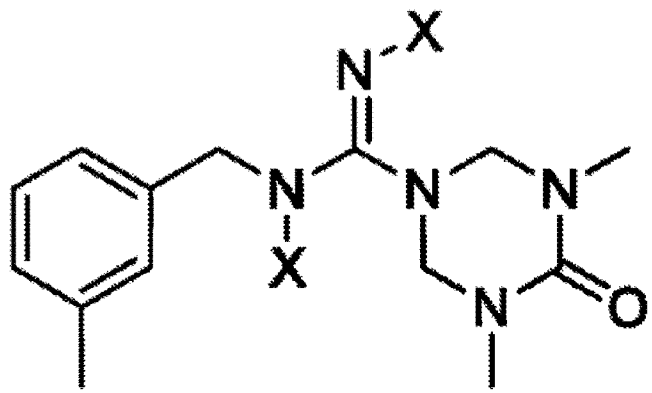

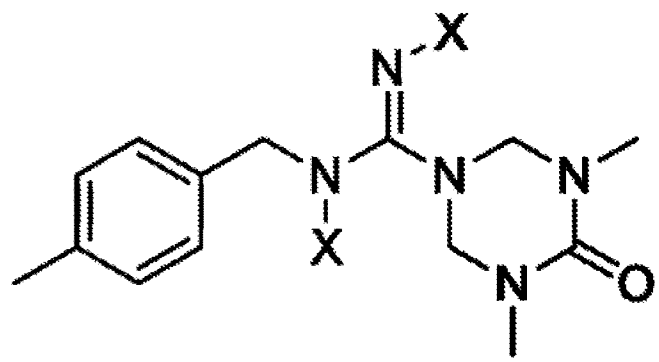

-- , therefor.

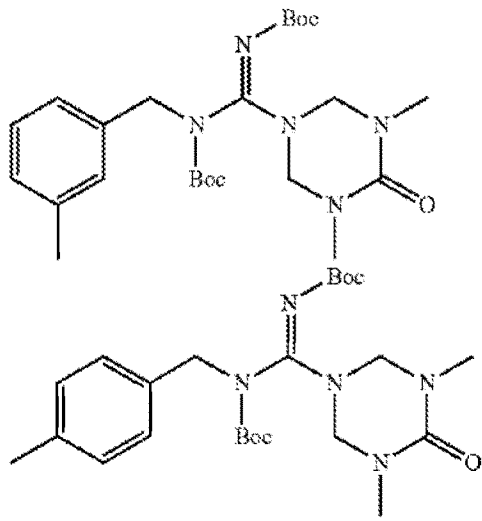

In Claim 12, Column 59, Lines 45-55, please delete " " and

CERTIFICATE OF CORRECTION (continued)
U.S. Pat. No. 10,053,423 B2 insert -- 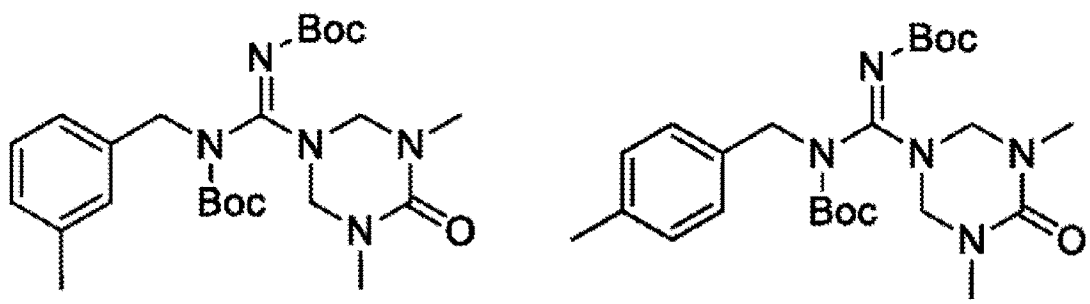 --, therefor.

In Claim 16, Column 66, Lines 25-35, please delete " 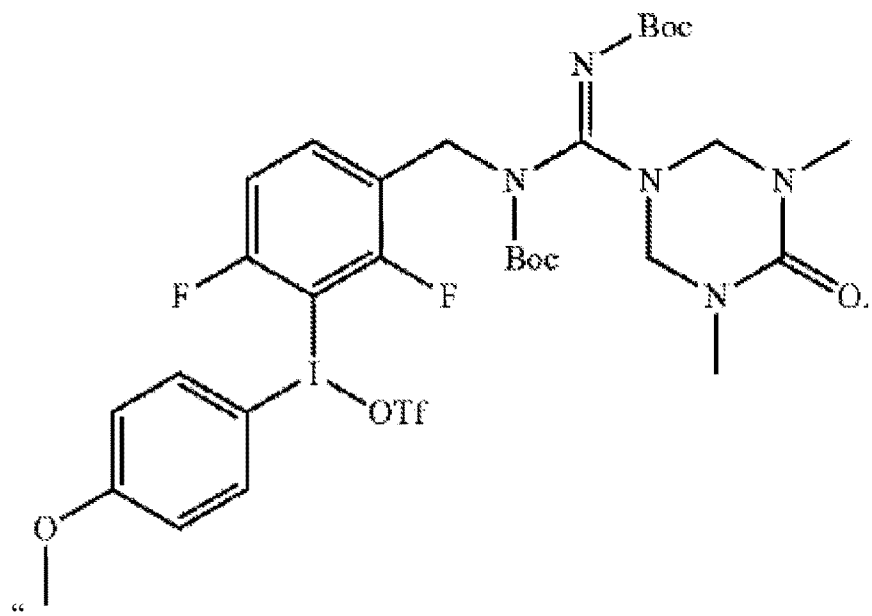 " and insert -- 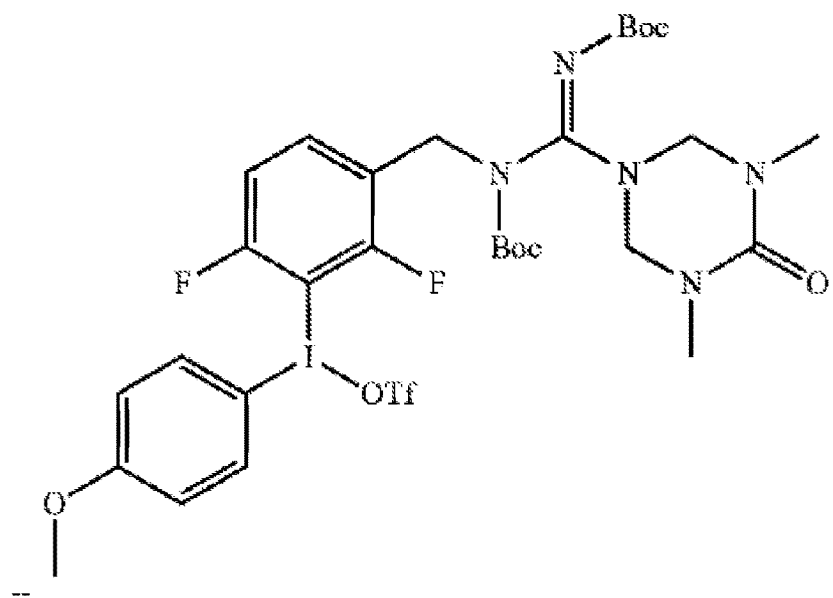 --, therefor.